(12) United States Patent
Zhan et al.

(10) Patent No.: US 9,421,269 B2
(45) Date of Patent: Aug. 23, 2016

(54) SAPONIN NANO MICELLE, PREPARING METHOD, APPLICATION AND PHARMACEUTICAL COMPOSITION THEREOF

(71) Applicant: FUJIAN SOUTH PHARMACEUTICAL CO., LTD, Sanming, Fujian (CN)

(72) Inventors: Huaxing Zhan, Shanghai (CN); Zhihong Jiang, Macao (CN); Dan Wang, Shanghai (CN); Xin Shen, Shanghai (CN); Jidong Yang, Shanghai (CN); Jianping Luo, Fujian (CN); Hongsheng Zhang, Yunnan (CN); Min Du, Fujian (CN); Pengfei Miao, Shanghai (CN)

(73) Assignee: FUJIAN SOUTH PHARMACEUTICAL CO., LTD., Fujian (CN)

( * ) Notice: Subject to any disclaimer, the term of this patent is extended or adjusted under 35 U.S.C. 154(b) by 38 days.

(21) Appl. No.: 14/370,885

(22) PCT Filed: Dec. 4, 2013

(86) PCT No.: PCT/CN2013/088558
§ 371 (c)(1),
(2) Date: Jul. 7, 2014

(87) PCT Pub. No.: WO2014/176900
PCT Pub. Date: Nov. 6, 2014

(65) Prior Publication Data
US 2015/0297727 A1    Oct. 22, 2015

(30) Foreign Application Priority Data

Apr. 28, 2013 (CN) .......................... 2013 1 0155639

(51) Int. Cl.
| | |
|---|---|
| *A01N 43/04* | (2006.01) |
| *A61K 31/70* | (2006.01) |
| *A61K 47/28* | (2006.01) |
| *A61K 31/7032* | (2006.01) |
| *A61K 31/7028* | (2006.01) |
| *A61K 8/63* | (2006.01) |
| *A61K 8/34* | (2006.01) |
| *A61K 8/49* | (2006.01) |
| *A61K 8/67* | (2006.01) |
| *A61Q 19/00* | (2006.01) |
| *A61K 8/14* | (2006.01) |
| *A61K 9/107* | (2006.01) |
| *A23L 1/30* | (2006.01) |
| *C07J 17/00* | (2006.01) |

(52) U.S. Cl.
CPC . *A61K 47/28* (2013.01); *A23L 1/30* (2013.01); *A23L 1/3002* (2013.01); *A61K 8/14* (2013.01); *A61K 8/347* (2013.01); *A61K 8/498* (2013.01); *A61K 8/4953* (2013.01); *A61K 8/63* (2013.01); *A61K 8/676* (2013.01); *A61K 9/1075* (2013.01); *A61K 31/7028* (2013.01); *A61K 31/7032* (2013.01); *A61Q 19/00* (2013.01); *C07J 17/005* (2013.01); *A61K 2800/413* (2013.01)

(58) Field of Classification Search
None
See application file for complete search history.

(56) References Cited

U.S. PATENT DOCUMENTS 5,977,081 A   11/1999  Marciani

FOREIGN PATENT DOCUMENTS

| CN | 1869055 A | 11/2006 |
|---|---|---|
| CN | 1869059 A | 11/2006 |
| CN | 101824065 A | 9/2010 |

(Continued)

OTHER PUBLICATIONS

Fuzzati Journal of Chromatography B (2004), vol. 812, pp. 119-133.*

(Continued)

*Primary Examiner* — Patrick Lewis
(74) *Attorney, Agent, or Firm* — Oliff PLC

(57) ABSTRACT

A saponin nano micelle, preparing method, application and pharmaceutical composition thereof is disclosed in the present invention. The saponin nano micelle comprises one or more of saponins represented by formula 1, in which, $R_1$ and $R_2$ are independently —H or a hydrophilic group, $R_3$ is —H or —OH, $R_4$ is a lipophilic group. The preparing method of the saponin nano micelle is that mixing the saponin with an organic solvent which can dissolve saponin, and then removing the organic solvent. The saponin micelle acts as a convey medium of the drug ingredients, and can replace conventional drug carriers such as pharmaceutical solubilizers or polymeric micelle, which has high safety and great significance. The pharmaceutical ingredients can prolong circulation time and biological half-life of drug in the blood, and increase the accumulation of drug in lesions, and reduce adverse reactions.

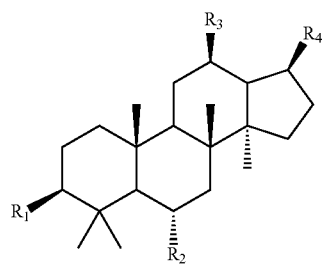

formula 1

34 Claims, 5 Drawing Sheets

(56) References Cited

FOREIGN PATENT DOCUMENTS

| | | |
|---|---|---|
| CN | 102174191 A | 9/2011 |
| CN | 102453072 A | 5/2012 |
| CN | 102603847 A | 7/2012 |
| CN | 102766187 A | 11/2012 |
| CN | 103271891 A | 9/2013 |
| EP | 2 815 746 A1 | 12/2014 |

OTHER PUBLICATIONS

Park et al. J. Korean Agricultural Chemical Society (1986), vol. 29, No. 2, pp. 198-206.*
Xiong et al. Journal of Pharmaceutics (2008), vol. 360, pp. 191-196.*
Riter et al. J. Phys. Chem. B (1997), vol. 101, pp. 8292-8297.*
Torchilin Pharmaceutical Research (2006), vol. 24, pp. 1-16.*
Pires et al. Biotechnol. Prog. (1993), vol. 9, pp. 647-650.*
Walthelm et al. Planta Med. (2001), vol. 67, pp. 49-54.*
Mar. 27, 2014 Search Report issued in International Application No. PCT/CN2013/088558.
Mar. 27, 2014 Written Opinion issued in International Application No. PCT/CN2013/088558.
Dai, Xingxing et al., "Mesoscopic Simulation Study on Influencing Factors on Micellization of Ginsenoside RO" Seminar: Chinese Medicine Information Engineering, Apr. 2012, vol. 14, No. 4, pp. 1767-1772, ISSN 1672-5433.
Li, Wenyuan et al,. "The Advance of Nano-Micelles Used As Drug Delivery". China Licensed Pharmacist, Dec. 2009, vol. 16, No. 12, pp. 36-39, ISSN 1672-5433.
May 26, 2014 Office Action issued in Chinese Application No. 201310155639.02.
Dai, Xingxing et al., "Multiscale Study on the Interaction Mechanism Between Ginsenoside Biosurfactant and Saikosaponin A". Journal of Colloid and Interface Science, vol. 396, p. 165-172, 2013.
Liu, Min et al., "Effects of Cellulose, Starch and Arginine on the Hydrolysis of Ginsenoside Rb1". Special Wild Economic Animal and Plant Research, Issue 1, pp. 38-40, 54. 2013.
Dec. 12, 2014 Office Action issued in Chinese Application No. 201310155639.2.
Japanese Patent Application No. 2015-514348.
Cao, Man et al. "Advances in Ginsenoside RH2 and Its Derivatives". World Science and Technology—Modernization of Traditional Chinese Medicine and Materia Medica, vol. 14, No. 6., pp. 2205-2211, 2012.
Liu, Mei et al. "Modification and Stability FO Ginsenoside RG1 PEG". China Journal of Chinese Materia Medica, vol. 37, Issue 10, May 2012, pp. 1378-1382.
Jun. 15, 2015 Office Action issued in Chinese Patent Application No. 201310155639.2.
Aug. 6, 2015 Extended European Search Report issued in European Patent Application No. 13870395.4.
Böttger, Stefan et al., "Saponins Can Perturb Biologic Membranes and Reduce the Surface Tension of Aqueous Solutions: A Correlation?". Bioorganic & Medicinal Chemistry, vol. 20, pp. 2822-2828, 2012.

\* cited by examiner

SAPONIN NANO MICELLE, PREPARING METHOD, APPLICATION AND PHARMACEUTICAL COMPOSITION THEREOF

The present application is the U.S. national stage application of International Application PCT/CN2013/088558, filed Dec. 4, 2013. The International Application claims priority of Chinese Patent Application 201310155639.2, filed Apr. 28, 2013, the contents of which are incorporated herein by reference in their entireties.

FIELD OF INVENTION

The present invention relates to the pharmaceutical field, specifically to a kind of saponin nano micelle, preparing method, application and pharmaceutical composition thereof.

PRIOR ARTS

A general characteristic of polymer micelles is amphipathicity, namely having both hydrophilic groups and hydrophobic groups simultaneously. The hydrophilic groups are always in the center of the polymer micelle to form a core and the hydrophobic groups are outside the polymer micelle to form a shell. The polymer which is formed by polymerization can form a polymeric micelle with drugs through wrapping lipid-soluble drug ingredients into the hydrophobic core of the polymer micelle, and dissolve in water or alcohol by their hydrophilic ends. Such a drug carried polymer micelle can prolong the cycling time of drugs in the blood and the biological half-life period, increase accumulation of the drug in lesions, reduce adverse reactions, connect with special carriers, antibodies or ligands to make them link to the receptors of target cells, and improve therapeutic effect. The previous studies on the application of micelles as drug carrier were mostly focused on polymer micelles and the representatives of these polymer micelles are poly-L-glutamic acid, poly-L-lysine, polysaccharides polymer chitin, polymer chitosan and etc.

However, in the previous studies, the effect of using polymer micelles as drug carriers to safely carry drug is unsatisfactory. The drug loading rate of polymer micelles is low, and the step of preparation of polymer micelles and drug loading is complicated, which limits the large-scale production. At the same time some synthetic materials are cytotoxic and also have many defects such as unsatisfactory target distribution that is difficult to meet the requirement of target, poor stability during the storage, probably increase of diameter of the micelle particles, occurrence of the drug degradation, and instant release phenomena during the release process. In order to solve the hydrophilic problem of lipid-soluble drugs, solubilizers or polymer micelles are always used. For example, some additives are added in cosmetics to dissolve the insoluble active ingredient, such as the most commonly used Tween 80 in Tween series, but these additives usually have certain toxicity and/or side effects. The lipophilic ingredients in Tween 80 include unsaturated fatty acids, which are easily oxidized in some circumstances and produce more toxic ingredients, and the produced toxins and side effects are likely to exceed the benefit brought by the product itself. It is confirmed in medical field that allergic reactions may be caused by the injection of Tween 80, which includes shock, dyspnea, hypotension, angioedema, rubella and etc. These adverse reactions may be very severe in human clinical trials, even death is reported. Therefore, the safe dosing of Tween 80 is restricted strictly in the drug, food and health care products. Other kinds of polymer micelles in the art also have the same problems more or less in the preparation, bioavailability and etc.

Thus, it is urgent and necessary to develop new safe and effective micelles with stronger drug-loading capacity and higher biological compatibility to solve the above mentioned problems. The phenomenon needs to be solved.

Saponin compounds include natural saponin compounds and artificial semisynthetic saponin compounds. Now, modification technology on natural saponin compounds such as ginsenoside and notoginsenoside is mature, and many semisynthetic saponin derivatives are obtained. For example, the invention application CN200910217947.7 and the publication No. CN101824065A, modifies the secondary glycosides Rh1 of ginsenoside; the invention application with the application No. CN201110054137.1 and the publication No. CN102174191A also discloses the modification method of saponin compounds, such as ginsenoside, by use of polyethylene glycol; the invention application with the application No. CN201010548971.1 and the publication No. CN102603847A discloses the preparation method of fatty acid ester compounds of ginsenoside Rh2; the invention application with the application No. CN201210207368.6 and the publication No. CN102766187A discloses tour kinds of ester derivatives of ginsenoside Compound-K and their preparation methods; "Modification and stability of ginsenoside Rg1 PEG" (Liu Mei, Wang Li, Hu Kaili, Feng Jianfang, China Journal of Chinese Materia Medica, Vol. 37, Issue 10, May 2012, 1378-1382) discloses the modification method of ginsenoside Rh1; "Advances in ginsenoside Rh2 and its derivatives" (Cao Man, Zhang Jie, Song Xinbo, Ma Baiping, World Science and Technology-Modernization of Traditional Chinese Medicine and Materia Medica, Vol. 14, No. 6, 2012) discloses ginsenoside Rh2 derivatives and their preparation methods.

Reverse micelle means an aggregate spontaneously formed by a certain number of amphiphilic substances in non-polar organic solvents (self-organized system), wherein the polar groups of the amphiphilic substances are toward the inside of the micelle, while the nonpolar groups are toward the continuous oil phase outside the micelle, the internal polar environment of reverse micelle can make water-soluble substances solubilized. Reverse micelle, as drug carrier, can increase the stability of drugs, and it can be transformed into liquid crystal structure after contacting with body fluids, so as to block the drug dissolution and to achieve sustained-release and controlled-release drug delivery. Reverse micelle also can be used as carrier of transdermal drug delivery system. Meanwhile, the reverse micelle can be used in nanoparticle preparation technology, and the prepared nanoparticles have the characteristics of small particle sizes and narrow particle distribution. The most commonly used reverse micelles are lecithin reverse micelle and sodium di-2-ethylhexyl sulfosuccinate (AOT) reverse micelle.

There are many reviews on segmented copolymer micelles and dendritic polymer micelles, but less study and literature about reverse micelles in pharmaceutics field. Especially, it is not mature to use reverse micelles as a sustained-release and controlled-release drug delivery system and reverse micelles in the aspects of drug releasing mechanism, pharmacokinetic characteristics and toxicology in animal, particularly in human, need further study and evaluation.

CONTENT OF THE PRESENT INVENTION

The present invention is to solve the technical problem that the lipid-soluble drugs are insoluble in water or the water-soluble drugs are insoluble in lipid system, and to overcome the existing problems that drug loading capacity of present polymer micelles or reverse micelles is unsatisfactory and the biocompatibility is poor, and provides a kind of saponin nano micelles, the preparing methods, application and pharmaceutical compositions thereof.

Through lots of experiments and repeated verifications, the inventors of the present invention found that, one or more of ginsenoside and/or notoginsenoside with certain structures, which can be from the roots, stems, leaves, fruits of Araliaceae, as well as artificially synthesized, can be made to prepare saponin nano micelles, which can be used as solubilizers or compound preparations of anti-tumor pharmaceutical ingredients, indissolvable cosmetic ingredients and indissolvable health food ingredients. Wherein, the positive micelle can be used as drug-loading micelle of lipid-soluble pharmaceutical ingredients which are indissolvable in water, and the used ginsenoside and/or notoginsenoside ingredients are natural and non-toxic, have no toxic and side effects, and the effect is excellent; at the same time, the reverse micelle prepared by those saponins can be used as solubilizers or compound preparations of water-soluble drugs or water-soluble ingredients, and also can be used as drug-loading micelle of water-soluble drugs or ingredients.

The present invention solves the above-mentioned technical problems through the following technical solutions.

The present invention provides a saponin nano micelle, which comprises one or more of saponins represented by formula 1;

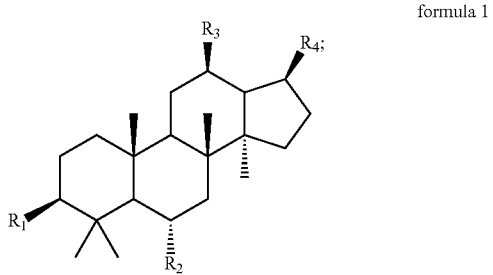

formula 1 wherein, $R_1$ and $R_2$ are independently —H or a hydrophilic group, $R_3$ is —H or —OH, $R_4$ is a lipophilic group.

In the present invention, the hydrophilic group is the common hydrophilic group in this field. Wherein, the hydrophilic group preferably is —OH, glycosyl, modified glycosyl, aliphatic acyl group, amino acid group, organic acid ester group or sulfate. Wherein, the modified glycosyl preferably is polymer modified glycosyl, aliphatic acyl group modified glycosyl, amino acid group modified glycosyl or organic acid ester group modified glycosyl.

In the present invention, $R_1$ and $R_2$ preferably are not —H at the same time.

In the present invention, more preferably, $R_1$ and $R_2$ are independently one of the following groups:

(1) —H, —OH; wherein, —H is hydrogen group, —OH is hydroxy group;

(2) $R_6$, wherein, $R_6$ is one of the following groups:
—O-Glc, —O-Rha, —O-Lyx, —O-Xyl, —O-Ara(p), —O-Ara(f), —O-Glc(2→1)Glc (the numbers represent carbon site, the same below), —O-Glc(6→1)Glc, —O-Glc(2→1)Rha, —O-Glc(2→1)Xyl, —O-Glc(6→1)Xyl, —O-Glc(6→1)Rha, —O-Glc(2→1)Ara(p), —O-Glc(6→1)Ara(p), —O-Glc(2→1)Ara(f), —O-Glc(6→1)Ara(f), —O-Glc(2→1)Glc(2→1)Glc, —O-Glc(2→1)Glc(2→1)Xyl, —O-Glc(6→1)Glc(6→1)Xyl, —O-Glc(2→1)Glc(4→1)Xyl, —O-Glc(2→1)Lyx, —O-Glc(6→1)Lyx, —O-Glc(2→1)Ara(p), —O-Glc(2→1)Glc(6→1)Glc, —O-Glc(2→1)Glc(6→1)Rha, —O-Glc(2→1)Glc(6→1)Xyl, —O-Glc(2→1)Glc(6→1)Lyx, —O-Glc(2→1)Glc(6→1)Ara(f), —O-Glc(2→1)Glc(6→1)Ara(p), —O-Glc(6→1)Glc(2→1)Glc, —O-Glc(6→1)Glc(2→1)Rha, —O-Glc(6→1)Glc(2→1)Xyl, —O-Glc(6→1)Glc(2→1)Lyx, —O-Glc(6→1)Glc(2→1)Ara(f), —O-Glc(6→1)Glc(2→1)Ara(p), —O-Glc(6→1)Glc(6→1)Glc, —O-Glc(6→1)Glc(6→-1)Rha, —O-Glc(6→1)Glc(6→1)Lyx, —O-Glc(6→1)Glc(6→1)Ara(f), —O-Glc(6→1)Glc(6→1)Ara(p);
wherein, Glc is glucopyranosyl, Xyl is xylopyranosyl, Rha is rhamnopyranosyl, Ara(p) is arabinopyranosyl, Ara(f) is arabinofuranosyl, Lyx is Lyxose group;

(3) $R_7$, $R_7$ is a group formed when no less than one of hydroxyl in $R_8$ is replaced by $R_5$; wherein, $R_5$ is one of the following groups:

I) -mPEG, —Z-mPEG, -mPEO, —Z-PEO, -mPVP, —Z-PVP, -mEPEG or —Z-EPEG; wherein, m is H, alkyl or acyl, Z is —CO(CH$_2$)$_a$CO—, —NH(CH$_2$)$_a$CO—, —NH(CH$_2$)$_b$X— or —CO—Ar—CH$_2$—; wherein. X is O, S or NH, Ar is aryl, a is an integer from 1 to 8, b is an integer from 1 to 10;

II) straight chain aliphatic acyl group of $C_4$~$C_{22}$, phosphate group, succinic acid ester group, n-butyl acid ester group, sulfonate group, malic acid ester group or sodium sulfate salt;

III) a group formed by dehydrogenizing carboxyl of one of Boc-glycine (Gly), Boc-alanine (Ala), Boc-Arginine (Arg). Boc-Lysine (Lys), Boc-Serine (Ser), Acetyl phenylalanine (Ac-Phe-OH), Acetyl-proline (Ac-Pro-OH), Acetyl phenylalanine (Ac-Phe-OH), Asparagine (Asn), Aspartic acid (Asp), Cysteine (Cys), Glutamine (Gln), Glutamic acid (Glu), Histidine (His), Isoleucine (Ile), Leucine (Leu), Methionine (Met), Phenylalanine (Phe), Proline (Pro), Threonine (Thr), Tryptophan (Trp), Tyrosine (Tyr) or Valine (Val);

(4) —O-PEO, —O-PVP, —O-PEG, —O-MPEG, —O-EPEG, —O-Glc (2→1)Glc(6→1)Mal or —O-Glc (2→1)Glc(6→1)Ac; wherein, Mal is malonyl, Ac is acetyl, PEG is polyethylene glycol, PEO is polyethylene, MPEG is end-monomethoxy polyethylene glycol, EPEG to end-epoxy polyethylene glycol, PVP is povidone;

(5) $R_8$, $R_8$ is one of the following groups:

I) -mPEG, —Z-mPEG, -mPEO, —Z-PEO, -mPVP, —Z-PVP, -mEPEG or —Z-EPEG; wherein, m is H, alkyl or acyl, Z is —CO(CH$_2$)$_a$CO—, —NH(CH$_2$)$_a$CO—, —NH(CH$_2$)$_b$X— or —CO—Ar—CH$_2$—; wherein, X is O, S or NH, Ar is an aryl, a is an integer from 1 to 8, b is an integer from 1 to 10;

II) straight chain aliphatic acyl group of $C_4$-$C_{22}$, phosphate group, succinic acid ester group, n-butyl acid ester group, sulfonate group, malic acid ester group or sodium sulfate salt;

III) a group formed by dehydrogenizing carboxyl of one of Boc-glycine (Gly), Boc-alanine (Ala), Boc-Arginine (Arg), Boc-Lysine (Lys), Boc-Serine (Ser), Acetyl phenylalanine (Ac-Phe-OH), Acetyl-proline (Ac-Pro-OH), Acetyl phenylalanine (Ac-Phe-OH), Asparagine (Asn), Aspartic acid (Asp), Cysteine (Cys), Glutamine (Gln), Glutamic acid (Glu), Histidine (His), isoleucine (Ile), Leucine (Leu), Methionine (Met), Phenylalanine (Phe), Proline (Pro), Threonine (Thr), Tryptophan (Trp), Tyrosine (Tyr) or Valine (Val);

and $R_1$ and $R_2$ are not —H at the same time.

Wherein, the molecular weight of the PEG, PEO, PVP and EPEG is preferably 200~2000 independently.

Wherein the straight chain aliphatic acyl group can be an acyl of natural saturated or unsaturated straight chain aliphatic acid, and an acyl of artificially synthesized saturated or unsaturated straight chain aliphatic acid, preferably is stearyl or palmityl.

Wherein, specifically, in —O-Glc-, the structure of Glc is:

in —O-Ara(p), the structure of Ara(p) is:

in —O-Lyx, the structure of Lyx is:

in —O-Ara(f), the structure of Ara(f) is in —O-Rha, the structure of Rha is:

in —O-Xyl, the structure of Xyl is:

the structure of Mal is:

Wherein, when $R_1$ and $R_2$ are independently $R_7$, $R_7$ is a group formed when no less than one of hydroxy in $R_6$ is replaced by $R_5$;

specifically, when $R_6$ is —O-Glc, —O-Rha, —O-Lyx, —O-Xyl, —O-Ara(p) or —O-Ara(f), $R_7$ preferably is a group formed when 1~4 hydroxyls in $R_6$ are replaced by the $R_5$;

when $R_6$ is —O-Glc(2→1)Glc, —O-Glc(6→1)Glc, —O-Glc(2→1)Rha, —O-Glc(2→1)Xyl, —O-Glc(6→1)Xyl, —O-Glc(6→1)Rha, —O-Glc(2→1)Ara (p), —O-Glc(6→1)Ara(p), —O-Glc(2→1)Ara(f), —O-Glc(6→1)Ara(f), —O-Glc(2→1)Lyx or —O-Glc(6→1)Lyx, $R_7$ preferably is a group formed when no less than one of hydroxyl in $R_6$ is replaced by $R_5$;

when $R_6$ is —O-Glc(2→1)Glc(4→1)Xyl, —O-Glc(2→1)Glc(2→1)Rha, —O-Glc(2→1)Glc(2→1)Lyx, —O-Glc(2→1)Glc(2→1)Ara(f), —O-Glc(2→1)Glc(2→1)Ara(p), —O-Glc(2→1)Glc(6→1)Glc, —O-Glc(2→1)Glc(6→1)Rha, —O-Glc(2→1)Glc(6→1)Xyl, —O-Glc(2→1)Glc(6→1)Lyx, —O-Glc(2→1)Glc(6→1)Ara(f), —O-Glc(2→1)Glc(6→1)Ara(p), —O-Glc(6→1)Glc(2→1)Glc, —O-Glc(6→1)Glc(2→1)Rha, —O-Glc(6→1)Glc(2→1)Xyl, —O-Glc(6→1)Glc(2→1)Lyx, —O-Glc(6→1)Glc(2→1)Ara(f), —O-Glc(6→1)Glc(2→1)Ara(p), —O-Glc(6→1)Glc(6→1)Glc, —O-Glc(6→1)Glc(6→1)Rha, —O-Glc(6→1)Glc(6→1)Lyx, —O-Glc(6→1)Glc(6→1)Ara(f), or —O-Glc(6→1)Glc(6→1)Ara(p), $R_7$ preferably is a group formed when no less than one of hydroxyl in $R_6$ is replaced by $R_5$;

In the present invention, the lipophilic group is the common lipophilic group in this field. In the present invention, $R_4$ preferably is the group represented by formula 2, formula 3 or formula 4:

formula 2 wherein, $R_9$, $R_{10}$ and $R_{11}$ are independently $C_1$~$C_3$ alkyl, d is an integer from 1~3:

formula 3 wherein, $R_{12}$, $R_{13}$ and $R_{14}$ are independently $C_1$~$C_3$ alkyl, e is an integer from 1~3:

formula 4 wherein, $R_{15}$ and $R_{16}$ are independently $C_1$~$C_3$ alkyl, f is an integer from 1~3.

In the present invention, $R_4$ most preferably is the group represented by formula 2-1, formula 3-1 or formula 4-1:

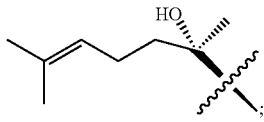

formula 2-1

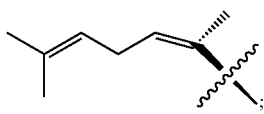

formula 3-1

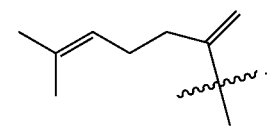

formula 4-1

In the present invention, preferably, in the saponin nano micelle, the saponins represented by formula 1 are type A saponin, type B saponin and type C saponin; or preferably, in the saponin nano micelle, the saponins represented by formula 1 are type B saponin and/or type C saponin; wherein the type A saponin is one or more of saponins represented by formula 1-1, the type B saponin is one or more of saponins represented by formula 1-2, and the type C saponin is one or more of saponins represented by formula 1-3:

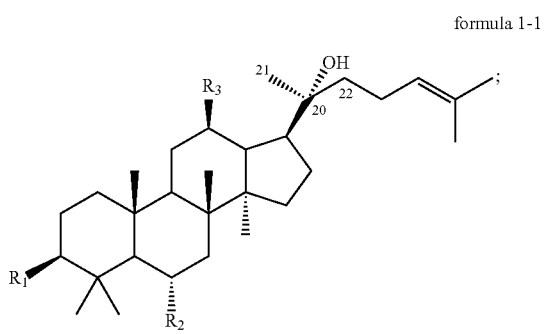

formula 1-1

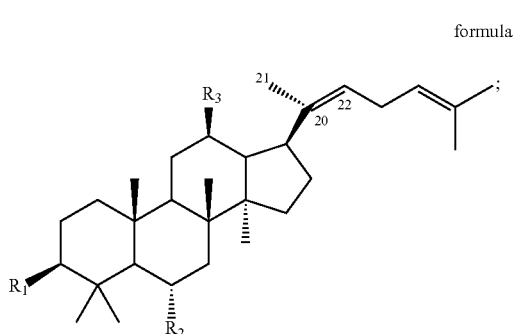

formula 1-2

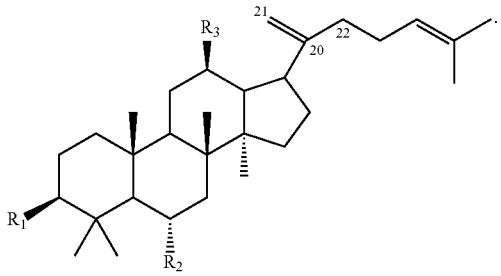

formula 1-3

Wherein, in the saponin nano micelle, when the saponins represented by formula 1 are the type A saponin, the type B saponin and the type C saponin, and the molar ratio of the type A saponin, the type B saponin and the type C saponin preferably is (0.8~1.2):(1.8~2.2):(0.8~1.2).

In the present invention, the most preferably, in the saponin nano micelle, the saponins represented by formula 1 are the type B saponin and/or the type C saponin, and the saponin nano micelle does not comprise the type A saponin.

The saponin nano micelle in the present invention can be divided into positive saponin nano micelle and reverse saponin nano micelle. Wherein, the positive saponin nano micelle has a characteristic of wrapping lipid-soluble pharmaceutical ingredient, and the reverse saponin nano micelle has a characteristic of wrapping water-soluble pharmaceutical ingredient.

In one of the saponin nano micelle of the present invention, when $R_2$ is —H or —OH and $R_1$ is the hydrophilic group except —OH in one or more of saponins represented by formula 1, the saponin nano micelle is positive saponin nano micelle, such as Rg5-type positive ginsenoside nano micelle, Rg5/Rk1-type positive ginsenoside nano micelle, Rg3/Rg5/Rk1-type positive ginsenoside nano micelle;

when $R_1$ is —H or —OH and $R_2$ is the hydrophilic group except —OH in one or more of saponins represented by formula 1, the saponin nano micelle is reverse saponin nano micelle, such as Rk4-type reverse ginsenoside nano micelle, Rk4/Rg6-type reverse ginsenoside nano micelle, Rg2/Rk4/Rg6-type reverse ginsenoside nano micelle;

when $R_1$ is incompletely —H or —OH, and $R_2$ is incompletely the hydrophilic group except —H and —OH in one or more of saponins represented by formula 1, the saponin nano micelle is positive saponin nano micelle, such as HSE-type positive ginsenoside nano micelle, Rg2/Rk4/Rg6-type positive ginsenoside nano micelle.

In the present invention, the saponin nano micelle can be formed by one or more saponins represented by formula 1. Hereinafter, the "mass content" refers to the mass percentages content that each substance accounts for the total mass of saponin micelle, and "molar content" refers to the molar percentages content that each substance accounts for the total molar of saponin micelle.

When the saponin nano micelle is formed by one kind of saponin represented by formula 1, the saponin is the type A saponin, the type B saponin or the type C saponin; the mass content of the saponin is no less than 70%, preferably is no less than 80%, more preferably is no less than 90%, the most preferably is no less than 95%. For example, according to the above saponin content, saponin nano micelle is formed respectively by ginsenoside Rg5, ginsenoside Rk1, ginsenoside Rk4, ginsenoside Rg6, wherein the ginsenoside nano micelle formed by ginsenoside Rg5 and ginsenoside Rk1 is positive ginsenoside nano micelle, and the ginsenoside nano micelle formed by ginsenoside Rk4 and ginsenoside Rg6 is reverse ginsenoside nano micelle.

Or, the saponin nano micelle is formed by the type B saponin or the type C saponin, the molar content of the saponin is no less than 70%, preferably is no less than 80%, more preferably is no less than 90%, the most preferably is no less than 95%.

When the saponin nano micelle is formed by two kinds of saponins represented by formula 1, namely the saponins are any two kinds of saponins in the type A saponin, the type B saponin and the type C saponin; a mass content of the two kinds of saponins is respectively no less than 25%, a total mass content of the two kinds of saponins is no less than 70%; preferably, a mass ratio of the two kinds of saponins is 0.8~1.2, and a total mass content of the two kinds of saponins is no less than 90%; more preferably, the mass ratio of the two kinds of saponins is 1:1, and the total mass content of the two kinds of saponins is no less than 95%. For example, according to the above saponin content, Rg5/Rk1-type positive ginsenoside nano micelle is formed by ginsenoside Rg5 and ginsenoside Rk1, and Rk4/Rk6-type reverse ginsenoside nano micelle is formed by ginsenoside Rk4 and ginsenoside Rg6.

Or, the saponin micelle is formed by the type B saponin and the type C saponin, a molar content of the type B saponin and the type C saponin is respectively no less than 25%, a total molar content of the type B saponin and the type C saponin is no less than 70%; preferably, a molar ratio of the type B saponin and the type C saponin is 0.8~1.2, and the total molar content of the type B saponin and the type C saponin is no less than 90%; more preferably, the molar ratio of the type B saponin and the type C saponin is 1:1, and the total molar content of the type B saponin and the type C saponin is no less than 95%.

When the saponin nano micelle is formed by three kinds of saponins represented by formula 1, namely the saponins are the type A saponin, the type B saponin and the type C saponin, a mass content of the type A saponin, the type B saponin and the type C saponin is respectively 15%~45%, and a total mass content of the type A saponin, the type B saponin and the type C saponin is no less than 70%;

preferably, the mass content of the type A saponin is 15%~25%, the mass content of the type B saponin is 35%~45%, the mass content of the type C saponin is 15%~25%, and the total mass content of the type A saponin, the type 13 saponin and the type C saponin is no less than 80%; more preferably, a mass ratio of the type A saponin, the type B saponin and the type C saponin is (0.8~1.2):(1.8~2.2):(0.8~1.2), and the total mass content of the type A saponin, the type B saponin and the type C saponin is no less than 90%; the most preferably, the mass ratio of the type A saponin, the type B saponin and the type C saponin is 1:2:1, and the total mass content of the type A saponin, the type B saponin and the type C saponin is no less than 95%.

For example, according to the content of the above saponin, Rg3/Rg5/Rk1-type positive ginsenoside nano micelle is formed by ginsenoside Rg3, ginsenoside Rg5 and ginsenoside Rk1, Rh2/Rh3/Rk2-type positive ginsenoside nano micelle is formed by ginsenoside Rh2, ginsenoside Rh3 and ginsenoside Rk2, and Rg2/Rk4/Rg6-type reverse ginsenoside nano micelle is formed by ginsenoside Rg2, ginsenoside Rk4 and ginsenoside Rg6. For another example, according to the content of the above saponin, the type A saponin: ginsenoside Rg2, ginsenoside Rg3, ginsenoside Rh1, the type B saponin: ginsenoside Rg5, ginsenoside Rk4, ginsenoside Rh4, and the type C saponin: ginsenoside Rk1, ginsenoside Rg6 and ginsenoside Rk3, together form into HSE-type positive ginsenoside nano micelle.

Or, the saponin micelle is formed by the type A saponin, the B saponin and the type C saponin, a molar content of the type A saponin, the type B saponin and the type C saponin is respectively 15%~45%, and a total molar content of the type A saponin, the type B saponin and the type C saponin is no less than 70%;

Preferably, the molar content of the type A saponin is 15%~25%, the molar content of the type B saponin is 35%~45%, the molar content of the type C saponin is 15%~25%, and the total molar content of the type A saponin, the type B saponin and the type C saponin is no less than 80%; more preferably, a molar ratio of the type A saponin, the type B saponin and the type C saponin is (0.8~2):(1.8~2.2):(0.8~1.2), and the total molar content of the type A saponin, the type B saponin and the type C saponin is no less than 90%; the most preferably, the molar ratio of the type A saponin, the type B saponin and the type C saponin is 1:2:1, and the total molar content of the type A saponin, the type B saponin and the type C saponin is no less than 95%.

In the present invention, the positive saponin nano micelle possesses amphipathicity as common polymer micelles, namely having both hydrophilic groups and hydrophobic groups. The core is formed by hydrophobic groups in the center, $R_1$ and/or $R_2$ is hydrophilic group, arranging outside the micelle to form the shell, the saponin nano micelle can form micelle with drugs through wrapping the lipid-soluble drug ingredient into the hydrophobic core of the micelle, and dissolve in water or alcohol by its hydrophilic ends. The positive saponin nano micelle can wrap lipid-soluble drug molecules into the interior of the micelle, prolong the cycling time of drug in the blood and the biological half-life period, increase the accumulation of drugs in the lesions, reduce adverse reactions, connect with special carriers, antibodies or ligands so as to make it bind to the receptors of target cells, and improve therapeutic effect.

In the present invention, the reverse saponin nano micelle possesses amphipathicity as common reveres polymer micelles, namely having both hydrophilic groups and hydrophobic groups. The core is formed by hydrophilic groups in the middle, $R_1$ and/or $R_2$ are hydrophilic groups, arranging inside the micelle to form the hydrophilic core, the saponin nano micelle can form reverse micelle with drugs through wrapping the water-soluble drug ingredient into the hydrophilic core of the micelle, and dissolve in ester or oil by its hydrophobic ends. The reverse saponin nano micelle can wrap water-soluble drug molecules into the interior of the micelle, prolong the cycling time of drug in the blood and the biological half-life period, increase the accumulation of drugs in the lesions, reduce adverse reactions, connect with special carriers, antibodies or ligands so as to make it hind to the receptors of target cells, and improve therapeutic effect.

In the present invention, the saponin represented by formula 1, mainly comes from raw materials of ginsenoside and/or notoginsenoside, such as ginsenoside, notoginsenoside and their analogs which are prepared from plants of Araliaceae or genus *Gynostemma* Bl. Cucurbitaceae. In the saponin nano micelle, except the saponins represented by formula 1, the rest of ingredients can be considered as unnecessary ingredients, and generally are inevitable impurities which usually are other types of ginsenoside and/or notoginsenoside except type A saponins, type B saponins and type C saponins, namely the compounds which are not represented by formula 1. Hereinafter, they will be explicitly referred as "other kinds of saponins".

Hereinafter, from the perspective that the saponin represented by formula 1 can be easily prepared through industrial production or in the laboratory, the most representative 8 kinds of saponin nano micelles are detailedly described as preferred embodiments. But the scope of the invention cannot be limited by these 8 kinds of saponin micelles.

The specific names and structures of ginsenoside represented by formula 1 referred by the following preferred embodiments 1 to 8 are involved as follows:

ginsenoside Rg5:

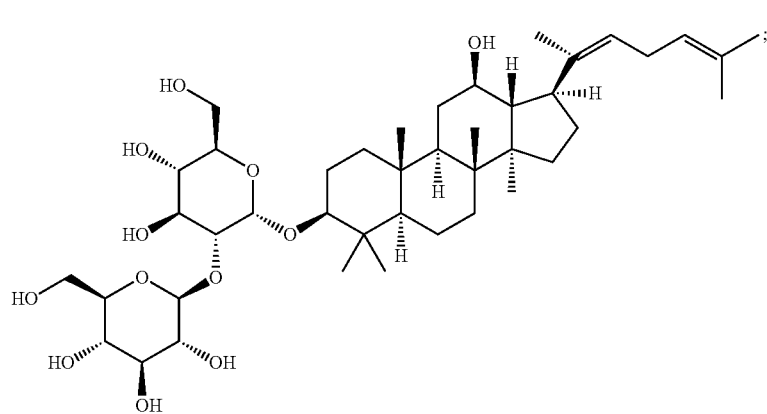

formula 5 ginsenoside Rk1:

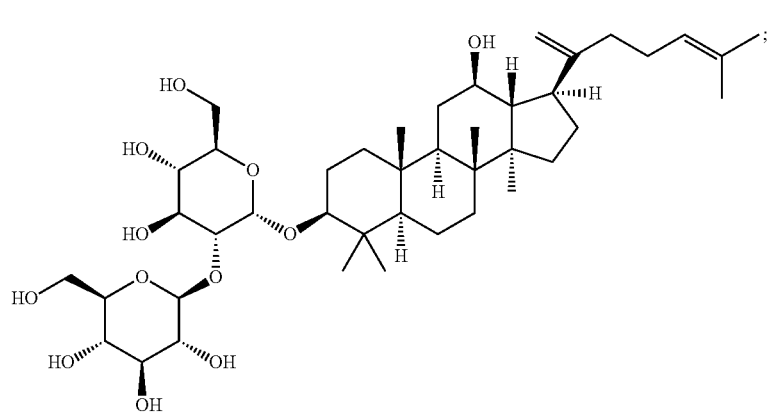

formula 6 ginsenoside Rg3:

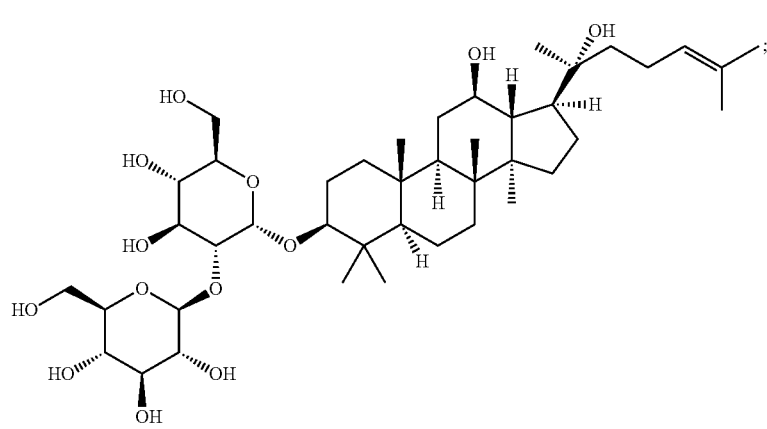

formula 7

-continued
ginsenoside Rh2:
formula 8
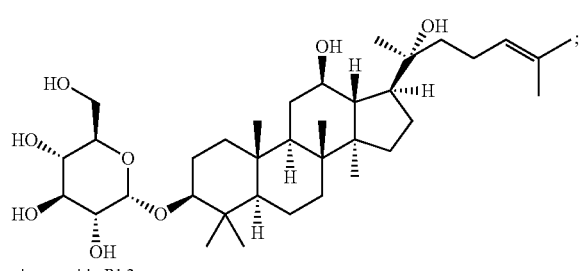
ginsenoside Rh3:
formula 9
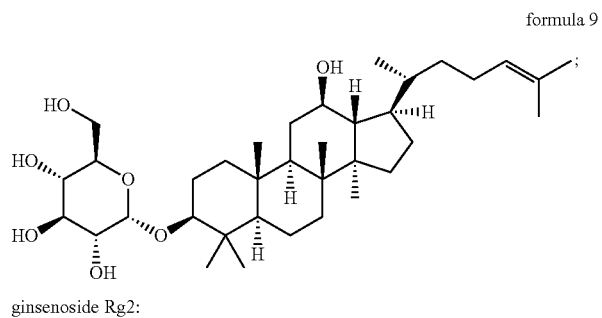
ginsenoside Rk2:
formula 10
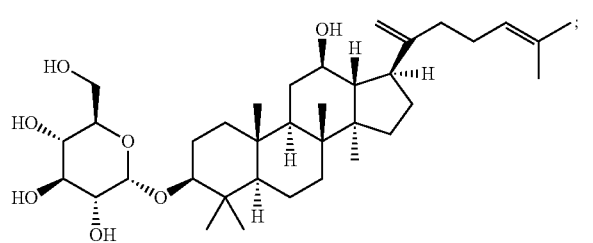
ginsenoside Rg2:
formula 11
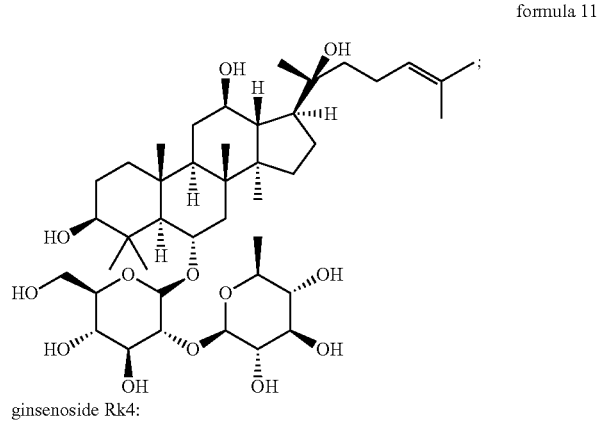
ginsenoside Rh1:
formula 12
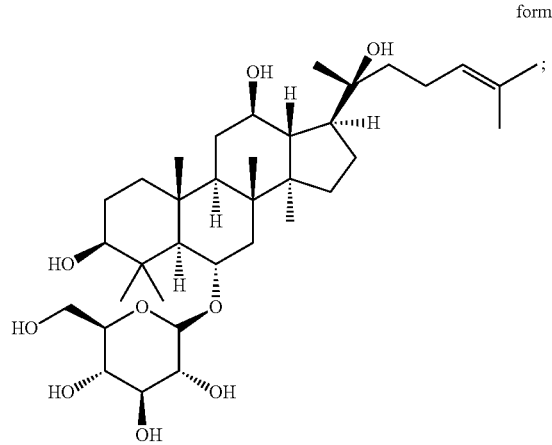
ginsenoside Rk4:
formula 13
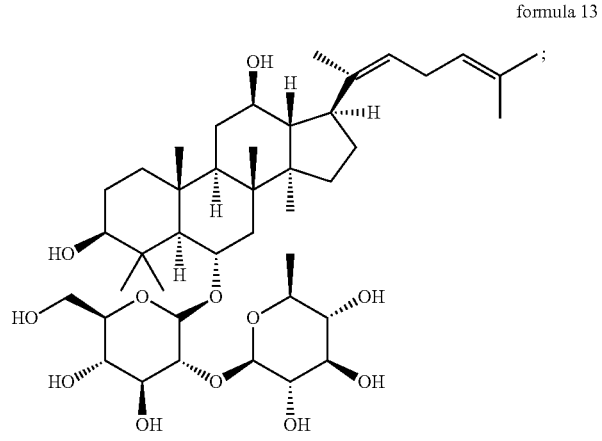
ginsenoside Rh4:
formula 14
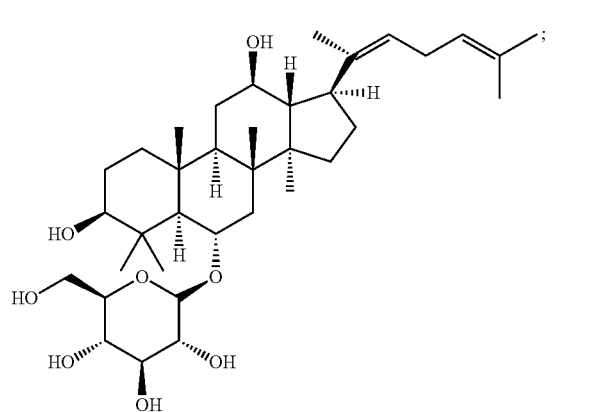
ginsenoside Rg6:
formula 15
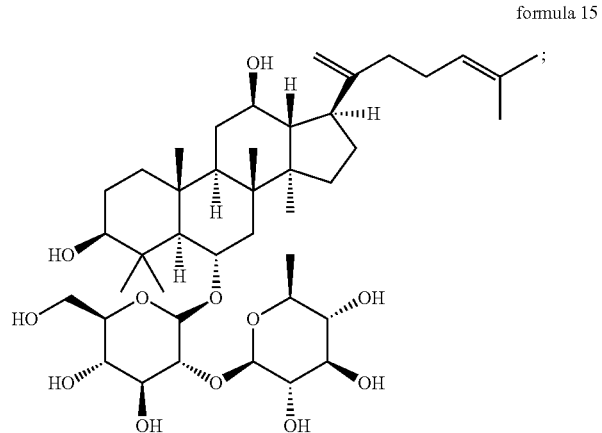

ginsenoside Rk3:

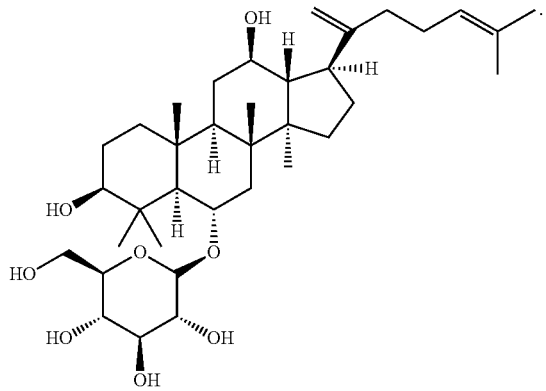

formula 16

-continued

In a preferred embodiment one of the present invention, the saponin nano micelle is Rg5-type positive ginsenoside nano micelle, which comprises ginsenoside Rg5, and a mass content of the ginsenoside Rg5 is no less than 50%.

Wherein, the mass content of the ginsenoside Rg5 preferably is no less than 70%, further preferably is no less than 85%, more preferably is no less than 90%, the most preferably is no less than 95%.

Or, the saponin nano micelle comprises ginsenoside Rg5, and a molar content of the ginsenoside Rg5 is no less than 50%, preferably is no less than 70%, further preferably is no less than 85%, more preferably is no less than 90%, the most preferably is no less than 95%.

Wherein, the ginsenoside Rg5 comes from the monomer ginsenoside Rg5 which is obtained by acidolysis and purification of the ginsenoside material mentioned above.

In the preferred embodiment one, except the ginsenoside Rg5, the rest of ingredients are other kinds of ginsenoside.

Besides ginsenoside Rg5, positive saponin nano micelles can also be formed by ginsenoside Rk1, ginsenoside Rs5, ginsenoside Rk2, ginsenoside Rh3, ginsenoside Rs4, or any one in the type B saponin and the type C saponin, in which $R_1$ is the hydrophilic group and $R_2$ is —H or —OH.

For example, in a modification embodiment of the preferred embodiment one of the present invention, the saponin nano micelle is Rk1-type positive ginsenoside nano micelle, including ginsenoside Rk1, and a mass content of the ginsenoside Rk1 is no less than 50%.

Wherein, the mass content of the ginsenoside Rk1 preferably is no less than 70%, further preferably is no less than 85%, more preferably is no less than 90%, the most preferably is no less than 95%.

Or, the saponin nano micelle comprises ginsenoside Rk1, and a molar content of the ginsenoside Rk1 is no less than 50%, preferably is no less than 70%, further preferably is no less than 85%, more preferably is no less than 90%, the most preferably is no less than 95%.

Wherein, the ginsenoside Rk1 comes from the monomer ginsenoside Rk1 which is obtained by acidolysis and purification of the ginsenoside material mentioned above.

In the preferred embodiment one, except the ginsenoside Rk1, the rest of ingredients are other kinds of ginsenoside.

In a preferred embodiment two of the present invention, the saponin nano micelle is Rk4-type reverse ginsenoside nano micelle, which comprises ginsenoside Rk4, and a mass content of ginsenoside Rk4 is no less than 50%.

Wherein, the mass content of ginsenoside Rk4 preferably is no less than 70%, further preferably is no less than 85%, more preferably is no less than 90%, the most preferably is no less than 95%.

Or, the saponin nano micelle comprises ginsenoside Rk4, and a molar content of ginsenoside Rk4 is no less than 50%, preferably is no less than 70%, further preferably is no less than 85%, more preferably is no less than 90%, the most preferably is no less than 95%.

Wherein, the ginsenoside Rk4 comes from the monomer ginsenoside Rk4 which is obtained by acidolysis and purification of the ginsenoside material mentioned above.

In the preferred embodiment two, except the ginsenoside Rk4, the rest of ingredients are other kinds of ginsenoside.

Besides the ginsenoside Rk4, reverse saponin nano micelles can also be formed by ginsenoside Rk3, ginsenoside F4, ginsenoside Rs7, ginsenoside Rh4, ginsenoside Rs6, notoginsenoside T5 or any one in the type B saponin and the type C saponin, in which $R_1$ is —H or —OH and $R_2$ is hydrophilic group.

For example, in a modification embodiment of the preferred embodiment two of the present invention, the saponin nano micelle is Rg6-type reverse ginsenoside nano micelle, which comprises ginsenoside Rg6, and a mass content of the ginsenoside Rg6 is no less than 50%.

Wherein, the mass content of the ginsenoside Rg6 preferably is no less than 70%, further preferably is no less than 85%, more preferably is no less than 90%, the most preferably is no less than 95%.

Or, the saponin nano micelle comprises ginsenoside Rg6, and a molar content of the ginsenoside Rg6 is no less than 50%, preferably is no less than 70%, further preferably is no less than 85%, more preferably is no less than 90%, the most preferably is no less than 95%.

Wherein, the ginsenoside Rg6 comes from the monomer ginsenoside Rg6 which is obtained by acidolysis and purification of the ginsenoside mentioned above.

In a modification embodiment of the preferred embodiment two, the rest of ingredients are other kinds of ginsenoside except the ginsenoside Rg6.

In a preferred embodiment three of the present invention, the saponin nano micelle is Rg5/Rk1-type positive ginsenoside nano micelle, which comprises ginsenoside Rg5 and ginsenoside Rk1, a mass content of the ginsenoside Rg5 is no less than 15%, a mass content of the ginsenoside Rk1 is no less than 15%, and a total mass content of the ginsenoside Rg5 and the ginsenoside Rk1 is no less than 50%.

Wherein, preferably, the mass content of the ginsenoside Rg5 is no less than 25%, the mass content of the ginsenoside Rk1 is no less than 25%, and the total mass of the ginsenoside Rg5 and the ginsenoside Rk1 is no less than 80%;

or, preferably, the mass content of the ginsenoside Rg5 is 25%~60%, the mass content of the ginsenoside Rk1 is 25%~60%, and the total mass content of the ginsenoside Rg5 and the ginsenoside Rk1 as no less than 70%;

further preferably, the mass content of the ginsenoside Rg5 is 35%~50%, the mass content of the ginsenoside Rk1 is 35%~50%, and the total mass content of the ginsenoside Rg5 and the ginsenoside Rk1 is no less than 80%;

more preferably, a mass ratio of the ginsenoside Rg5 and the ginsenoside Rk1 is 0.8~1.2, and the total mass content of the ginsenoside Rg5 and the ginsenoside Rk1 is no less than 80%;

further preferably the mass ratio of the ginsenoside Rg5 and the ginsenoside Rk1 is 0.8~1.2, and the total mass content of the ginsenoside Rg5 and the ginsenoside Rk1 is no less than 90%;

the most preferably, the total mass ratio of the ginsenoside Rg5 and the ginsenoside Rk1 is 1:1, and the total mass content of the ginsenoside Rg5 and the ginsenoside Rk1 is no less than 95%.

Or, the saponin nano micelle comprises ginsenoside Rg5 and ginsenoside Rk1, a molar content of the ginsenoside Rg5 is no less than 15%, a molar content of the ginsenoside Rk1 is no less than 15%, and a total molar content of the ginsenoside Rg5 and the ginsenoside Rk1 is no less than 50%.

Wherein, preferably, the molar content of the ginsenoside Rg5 is no less than 25%, the molar content of the ginsenoside Rk1 is no less than 25%, and the total molar content of the ginsenoside Rg5 and the ginsenoside Rk1 is no less than 80%;

or, preferably, the molar content of the ginsenoside Rg5 is 25%~60%, the molar content of the ginsenoside Rk1 is 25%~60%, and the total molar content of the ginsenoside Rg5 and the ginsenoside Rk1 is no less than 70%;

further preferably, the molar content of the ginsenoside Rg5 is 35%~50%, the molar content of the ginsenoside Rk1 is 35%~50%, and the total molar content of the ginsenoside Rg5 and the ginsenoside Rk1 is no less than 80%;

more preferably, a molar ratio of the ginsenoside Rg5 and the ginsenoside Rk1 is 0.8~1.2, and the total molar content of the ginsenoside Rg5 and the ginsenoside in Rk1 is no less than 80%;

further preferably, the molar ratio of the ginsenoside Rg5 and the ginsenoside Rk1 is 0.8~1.2, and the total molar content of the ginsenoside Rg5 and the ginsenoside Rk1 is no less than 90%;

the most preferably the molar ratio of the ginsenoside Rg5 and the ginsenoside Rk1 is 1:1 and the total molar content of the ginsenoside Rg5 and the ginsenoside Rk1 is no less than 95%.

In the preferred embodiment three, except the ginsenoside Rg5 and the ginsenoside Rk1, the rest of ingredients are other kinds of ginsenoside.

Besides ginsenoside Rg5 and ginsenoside Rk1, positive saponin nano micelles can also be formed by any two in the type B saponin and type C saponin, in which $R_1$ is hydrophilic group and $R_2$ is —H or —OH.

In a preferred embodiment four of the present invention, the saponin nano micelle is Rk4/Rg6 type reverse ginsenoside nano micelle, which comprises ginsenoside Rk4 and ginsenoside Rg6, a mass content of the ginsenoside Rk4 is no less than 15%, the mass content of the ginsenoside Rg6 is no less than 15%, and a total mass content of the ginsenoside Rk4 and the ginsenoside Rg6 is no less than 50%.

Wherein, preferably, the mass content of the ginsenoside Rk4 is 25%~60%, the mass content of the ginsenoside Rg6 is 25%~60%, and the total mass content of the ginsenoside Rk4 and the ginsenoside Rg6 is no less than 70%;

further preferably, the mass content of ginsenoside Rk4 is 35%~50%, the mass content of the ginsenoside Rg6 is 35%~50%, and the total mass of content of the ginsenoside Rk4 and the ginsenoside Rg6 is no less than 80%;

more preferably, a mass ratio of the ginsenoside Rk4 and the ginsenoside Rg6 is 0.8~1.2, and the total mass content of the ginsenoside Rk4 and the ginsenoside Rg6 is no less than 90%;

the most preferably, the mass ratio of the ginsenoside Rk4 and the ginsenoside Rg6 is 1:1, and the total mass content of the ginsenoside Rk4 and the ginsenoside Rg6 is no less than 95%.

Or, the saponin nano micelle comprises ginsenoside Rk4 and ginsenoside Rg6, a molar content of the ginsenoside Rk4 is no less than 15%, the molar content of the ginsenoside Rg6 is no less than 15%, and the total molar content of the ginsenoside Rk4 and ginsenoside Rg6 is no less than 50%.

Wherein, preferably, the molar content of the ginsenoside Rk4 is 25%~60%, the molar content of the ginsenoside Rg6 is 25%~60%, and the total molar content of the ginsenoside Rk4 and the ginsenoside Rg6 is no less than 70%;

further preferably, the molar content of the ginsenoside Rk4 is 35%~50%, the molar content of the ginsenoside Rg6 is 35%~50%, and the total molar content of the ginsenoside Rg6 and the ginsenoside Rk4 is no less than 80%;

more preferably, a molar ratio of the ginsenoside Rk4 and the ginsenoside Rg6 is 0.8~1.2, and the total molar content of the ginsenoside Rk4 and the ginsenoside Rg6 is no less than 90%;

the most preferably, the molar ratio of the ginsenoside Rk4 and the ginsenoside Rg6 is 1:1, and the total molar content of the ginsenoside Rk4 and the ginsenoside Rg6 is no less than 95%.

In the preferred embodiment four, except the ginsenoside Rk4 and the ginsenoside Rg6, the rest of ingredients are other kinds of ginsenoside.

Besides ginsenoside Rk4 and ginsenoside Rg6, reverse saponin nano micelles can also be formed by any two in the type B saponin and die type C saponin, in which $R_1$ is —H or —OH and $R_2$ is hydrophilic group.

In a preferred embodiment five of the present invention, the saponin nano micelle is Rg3/Rg5/Rk1 type positive ginsenoside nano micelle, which comprises ginsenoside Rg3, ginsenoside Rg5 and ginsenoside Rk1, a mass content of the ginsenoside Rg3 is 15%~5%, a mass content of the ginsenoside Rg5 is 15%~45%, a mass content of the ginsenoside Rk1 is 15%~45%, and a total mass content of the ginsenoside Rg3, the ginsenoside Rg5 and the ginsenoside Rk1 is no less than 70%.

Wherein, preferably the mass content of the ginsenoside Rg3 is 15%~25%, the mass content of the ginsenoside Rg5 is from 35%~45%, the mass content of the ginsenoside Rk1 is 15%~25%, and the total mass content of the ginsenoside Rg3, the ginsenoside Rg5 and the ginsenoside Rk1 is no less than 80%;

more preferably, a mass ratio of the ginsenoside Rg3, the ginsenoside Rg5 and the ginsenoside Rk1 is (0.8~1.2):(1.8~2.2):(0.8~1.2), and the total mass content of the ginsenoside Rg3, the ginsenoside Rg5 and the ginsenoside Rk1 is 90%;

the most preferably, the mass ratio of the ginsenoside Rg3, the ginsenoside Rg5 and the ginsenoside Rk1 is 1:2:1.

Or, the saponin nano micelle comprises ginsenoside Rg3, ginsenoside Rg5 and ginsenoside Rk1, a molar content of the ginsenoside Rg3 is 15%~45%, a molar content of the ginsenoside Rg5 is 15%~45%, a molar content of the ginsenoside Rk1 is 15%~45%, and a total molar content of the ginsenoside Rg3, the ginsenoside Rg5 and the ginsenoside Rk1 is no less than 70%.

Wherein, preferably, the molar content of the ginsenoside Rg3 is 15%~25%, the molar content of the ginsenoside Rg5 is 35%~45%, the molar content of the ginsenoside Rk1 is 15%~25%, and the total molar content of the ginsenoside Rg3, the ginsenoside Rg5, and the ginsenoside Rk1 is no less than 80%;

more preferably, a molar ratio of the ginsenoside Rg3, the ginsenoside Rg5 and the ginsenoside Rk1 is (0.8~1.2):(1.8~2.2):(0.8~1.2), and the total molar content of the ginsenoside Rg3, the ginsenoside Rg5 and the ginsenoside Rk1 is 90%;

the most preferably, the molar ratio of the ginsenoside Rg3, the ginsenoside Rg5 and the ginsenoside Rk1 is 1:2:1.

In the preferred embodiment five, except the ginsenoside Rg3, the ginsenoside Rg5 and the ginsenoside Rk1, the rest of ingredients are other kinds of ginsenoside.

In a preferred embodiment six of the present invention, the saponin nano micelle is Rh2/Rh3/Rk2-type positive ginsenoside nano micelle, which comprises ginsenoside Rh2, ginsenoside Rh3 and ginsenoside Rk2, a mass content of the ginsenoside Rh2 is 15%~45%, a mass content of the ginsenoside Rh3 is 15%~45%, a mass content of the ginsenoside Rk2 is 15%~45%, and a total mass content of the ginsenoside Rh2, the ginsenoside Rh3 and the ginsenoside Rk2 is no less than 70%.

Wherein, preferably, the mass content of the ginsenoside Rh2 is 15%~25%, the mass content of the ginsenoside Rh3 is 35%~45%, the mass content of the ginsenoside Rk2 is 15%~25%, and the total mass content of the ginsenoside Rh2, the ginsenoside Rh3 and the ginsenoside Rk2 is no less than 80%;

more preferably, a mass ratio of the ginsenoside Rh2, the ginsenoside Rh3 and the ginsenoside Rk2 is (0.8~1.2):(1.8~2.2):(0.8~1.2), and the total mass content of the ginsenoside Rh2, the ginsenoside Rh3 and the ginsenoside Rk2 is no less than 90%;

the most preferably, the mass ratio of the ginsenoside Rh2, the ginsenoside Rh3 and the ginsenoside Rk2 is 1:2:1.

Or, the saponin nano micelle comprises ginsenoside Rh2, ginsenoside Rh3 and ginsenoside Rk2, a molar content of the ginsenoside Rh2 is 15%~45%, the molar content of the ginsenoside Rh3 is 15%~45%, a molar content of ginsenoside Rk2 is 15%~45%, and a total molar content of the ginsenoside Rh2, the ginsenoside Rh3 and the ginsenoside Rk2 is no less than 70%.

Wherein, preferably, the molar content of the ginsenoside Rh2 is 15%~25%, the molar content of the ginsenoside Rh3 is 35%~45%, the molar content of the ginsenoside Rk2 is 15%~25%, and the total molar content of the ginsenoside Rh2, the ginsenoside Rh3 and the ginsenoside Rk2 is no less than 80%;

more preferably, a molar ratio of the ginsenoside Rh2, the ginsenoside Rh3 and the ginsenoside Rk2 is (0.8~1.2):(1.8~2 2):(0.8~1.2), and the total molar content of the ginsenoside Rh2, the ginsenoside Rh3 and the ginsenoside Rk2 is no less than 90%;

the most preferably, the molar ratio of the ginsenoside Rh2, the ginsenoside Rh3 and the ginsenoside Rk2 is 1:2:1.

In the preferred embodiment six, except the ginsenoside Rh2, the ginsenoside Rh3 and the ginsenoside Rk2, the rest of ingredients are other kinds of ginsenoside.

In a preferred embodiment seven of the present invention, the saponin nano micelle is Rg2/Rk4/Rg6-type ginsenoside micelle, which comprises ginsenoside Rg2, ginsenoside Rk4 and ginsenoside Rg6, a mass content of the ginsenoside Rg2 is 15%~45%, a mass content of the ginsenoside Rk4 is 15%~45%, a mass content of the ginsenoside Rg6 is 15%~45%, and a total mass content of the ginsenoside Rg2, the ginsenoside Rk4 and the ginsenoside Rg6 is no less than 70%.

Wherein, preferably, the mass content of the ginsenoside Rg2 is 15%~25%, the mass content of the ginsenoside Rk4 is 35%~45%, the mass content of the ginsenoside Rg6 is 15%~25%, and the total mass content of the ginsenoside Rg2, the ginsenoside Rk4 and the ginsenoside Rg6 is no less than 80%;

more preferably, a mass ratio of the ginsenoside Rg2, the ginsenoside Rk4 and the ginsenoside Rg6 is (0.8~1.2):(1.8~2 2):(0 8~1.2), and the total mass content of the ginsenoside Rg2, the ginsenoside Rk4 and the ginsenoside Rg6 is no less than 90%;

the most preferably, the mass ratio of the ginsenoside Rg2, the ginsenoside Rk4 and the ginsenoside Rg6 is 1:2:1, and the total mass content of the ginsenoside Rg2, the ginsenoside Rk4 and the ginsenoside Rg6 is no less than 95%.

Or, the saponin nano micelle comprises ginsenoside Rg2, ginsenoside Rk4 and ginsenoside Rg6, a molar content of the ginsenoside Rg2 is 15%~45%, a molar content of the ginsenoside Rk4 is 15%~45%, a molar content of the ginsenoside Rg6 is 15%~45%, and a total molar content of the ginsenoside Rg2, the ginsenoside Rk4 and the ginsenoside Rg6 is no less than 70%.

Wherein, preferably, the molar content of the ginsenoside Rg2 is 15%~25%, the molar content of the ginsenoside Rk4 is 35%~45%, the molar content of the ginsenoside Rg6 is 15%~25%, and the total molar content of the ginsenoside Rg2, the ginsenoside Rk4 and the ginsenoside Rg6 is no less than 80%;

more preferably, a molar ratio of the ginsenoside Rg2, the ginsenoside Rk4 and the ginsenoside Rg6 is (0 8~1.2):(1.8~2.2):(0.8~1.2), and the total molar content of the ginsenoside Rg2, the ginsenoside Rk4 and the ginsenoside Rg6 is no less than 90%;

the most preferably, the molar ratio of the ginsenoside Rg2, the ginsenoside Rk4 and the ginsenoside Rg6 is 1:2:1, and the total molar content of the ginsenoside Rg2, the ginsenoside Rk4 and the ginsenoside Rg6 is no less than 95%.

In the preferred embodiment seven, except the ginsenoside Rg2, the ginsenoside Rk4 and the ginsenoside Rg6. In this case, the Rg2/Rk4/Rg6-type ginsenoside nano micelle is Rg2/Rk4/Rg6-type reverse ginsenoside nano micelle, the rest of ingredients are other kinds of ginsenoside.

Specifically, when Rg2/Rk4/Rg6-type ginsenoside micelle comprises the saponin represented by formula 1, which can form positive micelle, for example, one or more of traces or ginsenoside Rg3, ginsenoside Rg5 and ginsenoside Rk1, the Rg2/Rk4/Rg6-type ginsenoside nano micelle is Rg2/Rk4/Rg6-type positive ginsenoside nano micelle.

In a preferred embodiment eight of the present invention, the saponin nano micelle is HSE-type ginsenoside nano micelle, which comprises ginsenoside Rg2, ginsenoside Rg3, ginsenoside Rh1, ginsenoside Rg5, ginsenoside Rk4, ginsenoside Rh4, ginsenoside Rk1, ginsenoside Rg6 and ginsenoside Rk3, wherein, a total mass content of the ginsenoside Rg2, the ginsenoside Rg3 and the ginsenoside Rh1 is 15%~45%, a total mass of the ginsenoside Rg5, the ginsenoside Rk4 and the ginsenoside Rh4 is 15%~45%, a total mass content of the ginsenoside Rk1, the ginsenoside Rg6 and the ginsenoside Rk3 is 15%~45%, and a total mass content of the ginsenoside Rg2, the ginsenoside Rg3, the ginsenoside Rh1, the ginsenoside Rg5, the ginsenoside Rk4, the ginsenoside Rh4, the ginsenoside Rk1, the ginsenoside Rg6 and the ginsenoside Rk3 is no less than 70%.

Wherein, preferably, the total mass content of the ginsenoside Rg2, the ginsenoside Rg3 and the ginsenoside Rh1 is 15%~25%, the total amass content of the ginsenoside Rg5, the ginsenoside Rk4 and the ginsenoside Rh4 is 35%~45%, the total mass content of the ginsenoside Rk1, the ginsenoside Rg6 and the ginsenoside Rk3 is 15%~25%, and the total mass content of the ginsenoside Rg2, the ginsenoside Rg3, the ginsenoside Rh1, the ginsenoside Rg5, the ginsenoside Rk4, the ginsenoside Rh4, the ginsenoside Rk1, the ginsenoside Rg6 and the ginsenoside Rk2 is no less than 80%;

more preferably, the mass ratio of the total mass of the ginsenoside Rg2, the ginsenoside Rg3 and the ginsenoside Rh1, the total mass of the ginsenoside Rg5, the ginsenoside Rk4 and the ginsenoside Rh4, and the total mass of the ginsenoside Rk1, the ginsenoside Rg6 and the ginsenoside Rk3 is (0.8~1.2):(1.8~2.2):(0.1~1.2), and the total mass content of the ginsenoside Rg2, the ginsenoside Rg3, the ginsenoside Rh1, the ginsenoside Rg5, the ginsenoside Rk4, the ginsenoside Rh4, the ginsenoside Rk1, the ginsenoside Rk3 and the ginsenoside Rg6 is no less than 95%;

the most preferably, the total mass ratio of the total mass of the ginsenoside Rg2, the ginsenoside Rg3 and the ginsenoside Rh1, the total mass or the ginsenoside Rg5, the ginsenoside Rk4 and the ginsenoside Rh4, and the total mass or the ginsenoside Rk1, the ginsenoside Rg6 and the ginsenoside Rk3 is 1:2:1.

Or, the saponin nano micelle comprises ginsenoside Rg2, ginsenoside Rg3, ginsenoside Rh1, ginsenoside Rg5, ginsenoside Rk4, ginsenoside Rh4, ginsenoside Rk1, ginsenoside Rg6 and ginsenoside Rk3, wherein, a total molar content of the ginsenoside Rg2, the ginsenoside Rg3 and the ginsenoside Rh1 is 15%~45%, a total molar of the ginsenoside Rg5, the ginsenoside Rk4 and the ginsenoside Rh4 is 15%~45%, a total molar content of the ginsenoside Rk1, the ginsenoside Rg6 and the ginsenoside Rk3 is 15%~4% and a total molar content of the ginsenoside Rg2, the ginsenoside Rg3, the ginsenoside Rh1, the ginsenoside Rg5, the ginsenoside Rk4, the ginsenoside Rh4, the ginsenoside Rk1, the ginsenoside Rg6 and the ginsenoside Rk3 is no less than 70%.

Wherein, preferably, the total molar content of the ginsenoside Rg2, the ginsenoside Rg3 and the ginsenoside Rh1 is 15%~25%, the total molar content of the ginsenoside Rg5, the ginsenoside Rk4 and the ginsenoside Rh4 is 35%~45%, the total molar content of the ginsenoside Rk1, the ginsenoside Rg6 and the ginsenoside Rk3 is 15%~25% and the total molar content of the ginsenoside Rg2, the ginsenoside Rg3, the ginsenoside Rh1, the ginsenoside Rg5, the ginsenoside Rk4, the ginsenoside Rh4, the ginsenoside Rk1, the ginsenoside Rg6 and the ginsenoside Rk3 is no less than 80%;

more preferably, a molar ratio of the total molar of the ginsenoside Rg2, the ginsenoside Rg3 and the ginsenoside Rh1, the total molar of the ginsenoside Rg5, the ginsenoside Rk4 and the ginsenoside Rh4, and the total molar of the ginsenoside Rk1, the ginsenoside Rg6 and the ginsenoside Rk3 is (0.9~1.2):(1.8~2.2):(0.8~1.2), and the total molar content of the ginsenoside Rg2, the ginsenoside Rg3, the ginsenoside Rh1, the ginsenoside Rg5, the ginsenoside Rk4, the ginsenoside Rh4, the ginsenoside Rk1 the ginsenoside Rg6 and the ginsenoside Rk3 is no less than 95%;

the most preferably, the total molar ratio of the total molar of the ginsenoside Rg2, the ginsenoside Rg3 and the ginsenoside Rh1, the total molar of the ginsenoside Rg5, the ginsenoside Rk4 and the ginsenoside Rh4, and the total molar of the ginsenoside Rk1, the ginsenoside Rg6 and the ginsenoside Rk3 is 1:2:1.

In the preferred embodiment eight, except the ginsenoside Rg2, the ginsenoside Rg3, the ginsenoside Rh1, the ginsenoside Rg5, the ginsenoside Rk4, the ginsenoside Rh4, the ginsenoside Rk1, the ginsenoside Rg6 and the ginsenoside Rk3, the rest of ingredients are other kinds of ginsenoside.

The present invention also provides a preparing method for saponin nano micelle, which comprises the following steps: mixing the saponin represented by formula 1 with an organic solvent which can dissolve saponin, and then removing the organic solvent.

Wherein, the organic solvent which can dissolve saponin can be the conventional organic solvent which is used to dissolve ginsenoside and/or notoginsenoside in this field, preferably is selected from a group consisting of methanol, ethanol, N,N-dimethylformamide (DMF), n-butanol, propanol, tetrahydrofuran and pyridine.

Wherein, the methods and conditions used for mixing can be the conventional methods and conditions used in this field, and are subject to the uniformity of mixing. The mixing temperature preferably is 30° C.~80° C.

Wherein, the methods and conditions used for removing the organic solvent can be the conventional methods and conditions used in this field. The way of removing the organic solvent preferably is concentration and drying under reduced pressure at 30° C.~9° C. The way of removing the organic solvent more preferably is: after the concentration and drying under reduced pressure, drying under vacuum at 30° C.~80° C. until the weight loss on drying is less than 3% mass percentage.

The present invention also provides a preparing method for saponin nano micelle, which comprises the following steps:

(1) using an extract of plant of Araliaceae and/or Cucurbitaceae as raw immaterial, carrying out acidolysis reaction in an acidic aqueous solution to obtain a reaction solution containing saponin mixture;

(2) after purifying to remove impurities in the reaction solution containing saponin mixture obtained in the step (1), mixing with an organic solvent which can dissolve saponin, and removing the organic solvent to obtain the saponin nano micelle;

or, purifying and separating the reaction solution containing saponin mixture obtained in the step (1) to obtain kinds of saponin monomers, mixing one or more of ginsenoside represented by formula 1 in the saponin monomers with an organic solvent which can dissolve saponin, and removing the organic solvent to obtain the saponin nano micelle.

In the step (1), the extract of plant of Araliaceae is the conventional plants described in this field, generally is the extract of one or more of root, stem, leave and fruit of plant of Araliaceae. The plant of Araliaceae preferably is selected from a group consisting of Chinese *ginseng* (*Panax ginseng*), Korean *ginseng* (*P. Sinensis J. Wen*), American *ginseng* (*P. quique folius*). Japanese *ginseng* (*P. japonicus*), Vietnamese *ginseng* (*P. vientnamensis*), *Panax* Pseudo-*ginseng* (*P. pseudoginseng*) and *Panax notoginseng* (*P. notoginseng*). The extract of plant of Cucurbitaceae is the conventional plant described in this field, generally is selected from a group consisting of root, stein, leave and fruit of plant of *Gynostemma* Bl. Cucurbitaceae. The plant of Cucurbitaceae preferably is fiveleaf *gynostemma* herb *Gynostemma pentaphyllum*).

In the step (1), the extract of plant of Araliaceae and/or Cucurbitaceae preferably satisfies the following conditions: a mass percentage content of total ginsenoside ≥60%, preferably ≥80%, more preferably ≥90%; or containing any one of the following ginsenoside with the mass content ≥60%, preferably ≥80%, more preferably ≥90%; ginsenoside Rb1, ginsenoside Rb2, ginsenoside Rb3, ginsenoside Re, ginsenoside Rc, ginsenoside Rd, ginsenoside Rg1, ginsenoside Rg2, ginsenoside Rg3, ginsenoside Rh1, ginsenoside Rh2, ginsenoside Rh3, ginsenoside F1, ginsenoside F2 and notoginsenoside R1, further preferably ginsenoside Rb1, ginsenoside Re or ginsenoside F2. The extract of plant of Araliaceae and/or Cucurbitaceae is commercially available or obtained according to the method described in the literature, such as the method according to CN200610093610.6.

In the step (1), the acidic aqueous solution can be the conventional solution described in this field, and the acidic compound in the acidic aqueous solution can be organic acid and/or inorganic acid, preferably is selected from a group consisting of citric acid, acetic acid, formic acid, oxalic acid, succinic acid, salicylic acid, tartaric acid, malic acid, citric acid, methanesulfonic acid, benzoic acid, hydrochloric acid, nitric acid, sulfuric acid and phosphoric acid, more preferably is acetic acid and/or citric acid.

In the step (1), the pH value of the acidic aqueous solution preferably is ≤6.5, further preferably is adjusted to ≤6.5 by acetic acid and/or citric acid; more preferably, the pH value of the acidic aqueous solution is ≤3, the most preferably is adjusted to ≤3 by acetic acid and/or citric acid.

In the step (1), the conditions of the acidolysis reaction can be the conventional conditions in this field. The temperature of the acidolysis reaction preferably is 60° C.~100° C., more preferably is 80° C.~90° C. The time of the acidolysis reaction preferably is 2 hours~48 hours, more preferably is 3 hours~6 hours.

In the step (2), the method of purifying to remove impurities can be the conventional methods described in this field, which only need to remove the impurities in the saponin reaction solution except saponin mixture, preferably, the method of purifying to remove impurities is one of the following method 1 or method 2;

The method 1 comprises the following steps:

(a) cooling the reaction solution containing saponin mixture obtained in the step (1), settling, and removing sediment;

(b) adjusting the pH of the reaction solution obtained by the step (a) to alkaline range by alkali to obtain a precipitate;

(c) mixing the precipitate and an organic solvent at 30° C.~80° C. to obtain a saponin mixture, the organic solvent is selected from a group consisting of methanol, ethanol, n-butanol, propanol tetrahydrofuran and pyridine;

(d) cooling the saponin mixture obtained in the step (c) to 5° C. below, removing sediment and drying.

In the step (a), the cooling and the settling are the conventional operations in this field, the cooling preferably is to cool to −20° C.~30° C., and the settling lime preferably is no less than 4 hours. The way of removing sediment is the conventional operation in this field, generally is filtration or centrifugation.

In the step (b), the alkali is the conventional alkali in this field, and can be organic base and/or inorganic base; the organic base preferably is selected from a group consisting of sodium methoxide, sodium ethoxide, potassium acetate, sodium acetate, triethylamine, ammonia, methanol amine, potassium tert-butoxide and sodium tert-butoxide, the inorganic base preferably is selected from a group consisting of sodium hydroxide, potassium hydroxide, calcium hydroxide, potassium carbonate, sodium carbonate, sodium bicarbonate and potassium bicarbonate, more preferably sodium carbonate and/or sodium bicarbonate. A concentration of the alkali in the reaction solution preferably is 0.05 mol/L~1 mol/L. The way of adjusting the pH to alkaline preferably is to adjust the pH to 8~14.

In the step (b), the precipitate preferably is dried by the conventional methods in this field, and then step (c) is conducted, and the way of drying is: drying at 30° C.~80° C. until the weight loss on drying is less than 5% mass percentage.

In the step (c), the usage of the organic solvent is the conventional usage in this field, preferably is an amount for dissolving the precipitate, more preferably, a volume ratio of the precipitate and the organic solvent is (1:1)~(1:5). The mixing temperature is preferably 30'C~80° C.

In the step (d), the cooling temperature is preferably −20° C.~5° C. The way of removing sediment is the conventional operation in this field, generally is filtration. The way of drying is the conventional method in this field, preferably is concentration and drying under reduced pressure.

The method 2 comprises the following steps:

S1. adjusting the pH of the reaction solution containing saponin mixture obtained in the step (1) to pH 8~14 by alkali, removing sediment to obtain solution A;

S2. extracting saponin in solution A obtained by the step S1 by n-butanol to obtain the n-butanol layer, then washing the n-butanol layer with water, and removing the solvent of the n-butanol layer.

In the step S1, the alkali is according to the alkali in the step (b).

In the step S2, the number of extraction times can be the conventional times in this field, preferably is 1~5 times. The volume ratio of the n-butanol and the solution A preferably is (1:0.5)~(1:4). The volume ratio of the n-butanol and the washing water preferably is (1:0.5)~(1:4). The operation of removing the solvent of the n-butanol layer is the conventional operation in this field, preferably is concentration and drying under reduced pressure.

In the step (2), the methods and conditions of purifying and separating are the conventional methods and conditions in this field, preferably is column chromatography.

In the step (2), the saponin monomer is selected from a group consisting of ginsenoside Rg2, ginsenoside Rg3, ginsenoside Rg4, ginsenoside Rg5, ginsenoside Rg6, ginsenoside Rh1, ginsenoside Rh2, ginsenoside Rh3, ginsenoside Rh4, ginsenoside Rf, ginsenoside Rs3, ginsenoside Rk1, ginsenoside Rk2, ginsenoside Rk3, ginsenoside Rk4, ginsenoside, ginsenoside F4, notoginsenoside R2 and notoginsenoside T5.

In the step (2), the organic solvent which can dissolve saponin preferably is selected from a group consisting of methanol, ethanol, N,N-dimethylformamide (DMF), n-butanol, propanol, tetrahydrofuran and pyridine. Wherein, the mixing is the conventional operation in this field, the mixing is subject to the uniformity of mixing. The mixing temperature preferably is 30° C.~80° C. The way of removing the organic solvent is the conventional method in this field, preferably is concentration and drying under reduced pressure at 30° C.~80° C.; more preferably is: after the concentration and drying under reduced pressure, drying under vacuum at 30° C.~80° C. until the weight loss on drying is less than 3% mass percentage.

In one preferred embodiment of the present invention, the preparing method for saponin nano micelle comprises the following steps:

(1') mixing acetic acid, water and an extract of plant of Araliaceae and/or Cucurbitaceae in which a mass content of saponin is more than 60%, the dosage of the acetic acid is 4 mL/g~6 mL/g extract of plant of Araliaceae and/or Cucurbitaceae, the concentration of the acid aqueous solution is 40%~60% by volume percent; and then carrying out reaction at 80° C.~90° C. for 3 hours~5 hours, after the reaction, cooling the reaction solution, settling for 4~24 hours and removing sediment;

(2') neutralizing the reaction solution treated in the step (1') with $Na_2CO_3$ and settling to obtain a precipitate;

(3') mixing the precipitate obtained in step (2') with absolute ethanol at 30° C.~80° C., and then cooling to 5° C. below, settling for 4 hours to 24 hours, removing sediment, and then concentrating under reduced pressure to obtain a concentrate; repeating the operation aforementioned in the step (3') for 1~3 times;

(4') and then drying the concentrate obtained in the step (3') to obtain the saponin nano micelle;

wherein, the saponin in step (1') is one of the saponin compounds as below: total ginsenoside Ra0, total ginsenoside Ra1, total ginsenoside Ra2, total ginsenoside Ra3, ginsenoside Rb1, ginsenoside Malonyl-Rb1, ginsenoside Rb2, ginsenoside Malonyl-Rb2, ginsenoside Rb3, ginsenoside Malonyl-Rb3, ginsenoside Rg1, ginsenoside Malonyl-Rg1, ginsenoside Re, ginsenoside Malonyl-Rc, ginsenoside F2, ginsenoside Re, ginsenoside Rd, ginsenoside Malonyl-Rd, American *ginseng* R1, ginsenoside Rs1, ginsenoside Rs2, notoginsenoside D, notoginsenoside K, notoginsenoside R1, notoginsenoside R3, notoginsenoside R4, notoginsenoside R6, notoginsenoside I, notoginsenoside Fa, notoginsenoside Fc, notoginsenoside Fd, notoginsenoside Fe, notoginsenoside T, notoginsenoside L, notoginsenoside O, notoginsenoside P, notoginsenoside Q, notoginsenoside S, gypenoside IX and gypenoside XVII. Wherein, ginsenoside Malonyl-Rg1 is malonyl ginsenoside Rg1. In the present invention, Malonyl also means malonyl.

When the saponin is total ginsenoside, the saponin nano micelle is HSE-type positive ginsenoside nano micelle; when the saponin is ginsenoside Rb1, the saponin nano micelle is Rg3-type positive ginsenoside nano micelle; when the saponin is ginsenoside F2, the saponin nano micelle is Rh2-type positive ginsenoside nano micelle; when the saponin is ginsenoside Re, the saponin nano micelle is Rg2-type reverse ginsenoside nano micelle.

In another preferred embodiment of the present invention, the preparing method of saponin nano micelle comprises the following steps:

(1") mixing citric acid, water and an extract of plant of Araliaceae and/or Cucurbitaceae in which a mass content of saponin is more than 60%, the dosage of the citric acid is 4 mL/g~6 mL/g extract of plant of Araliaceae and/or Cucurbitaceae, the concentration of the citric acid aqueous solution is 40%~60% by volume percent, and then carrying out reaction at 80° C.~90° C. for 3 hours~6 hours;

(2") cooling the reaction solution obtained from the step (1") to 15° C.~30° C., neutralizing the reaction solution with $Na_2CO_3$ and removing sediment to obtain solution A;

(3") mixing the solution A obtained in the step (2"), water and n-butanol, extracting and separating for 1~4 times;

(4") washing the n-butanol layer obtained in the step (3") with water for 1~3 times, concentrating under reduced pressure to obtain a solid;

(5") mixing the solid obtained in the step (4") with absolute ethanol at 5° C.~65° C., and then cooling to 5° C. below, settling for 4 hours~24 hours, removing sediment, and then concentrating under reduced pressure to obtain a concentrate; repeating the operation aforementioned in the step (5") for 1~3 times;

(6") drying the concentrate obtained in the step (5") to obtain the saponin nano micelle;

the saponin in the step (1") is one of the saponin compounds below: total ginsenoside Ra0, total ginsenoside Ra1, total ginsenoside Ra2, total ginsenoside Ra3, ginsenoside Rh1, ginsenoside Malonyl-Rb1, ginsenoside Rb2, ginsenoside Malonyl-Rb2, ginsenoside Rb3, ginsenoside Malonyl-Rb3, ginsenoside Rg1, ginsenoside Malonyl-Rg1, ginsenoside Rc, ginsenoside Malonyl-Rc, ginsenoside F2, ginsenoside Re, ginsenoside Rd, ginsenoside Malonyl-Rd, American *ginseng* R1, ginsenoside Rs1, ginsenoside Rs2, notoginsenoside D, notoginsenoside K, notoginsenoside R1, notoginsenoside R3, notoginsenoside R4, notoginsenoside R6, notoginsenoside I, notoginsenoside Fa, notoginsenoside Fc, notoginsenoside Fd, notoginsenoside Fe, notoginsenoside T, notoginsenoside L, notoginsenoside O, notoginsenoside P, notoginsenoside Q, notoginsenoside S, gypenoside IX and gypenoside XVII.

When the saponin is total saponin, the saponin nano micelle is HSE-type positive ginsenoside nano micelle; when the saponin is ginsenoside Rb1, the saponin nano micelle is Rg3-type positive ginsenoside nano micelle; when the saponin is ginsenoside F2, the saponin nano micelle is Rh2-type positive ginsenoside nano micelle; when the saponin is ginsenoside Re, the saponin nano micelle is Rg2-type reverse ginsenoside nano micelle.

The present invention also provides a saponin nano micelle prepared by the preparing methods mentioned above.

The present invention also provides a preparing method for positive saponin nano micelle, which comprises the following steps:

mixing reverse saponin nano micelle, an organic solvent which can dissolve saponin and a crystal seed of positive saponin nano micelle, removing the organic solvent to obtain the positive saponin nano micelle; wherein, the crystal seed of the positive saponin nano micelle is one or more of saponin represented by formula 1 in which $R_2$ is —H or —OH, and $R_1$ is hydrophilic group; the reverse saponin nano micelle is one or more of the reverse saponin nano micelle prepared by the preparing method mentioned above and the reverse saponin nano micelles mentioned above.

Wherein, in the crystal seed of the positive saponin nano micelle, R1 is preferably a glycosyl or a modified glycosyl, more preferably is one of the aforementioned, more preferable and specific $R_1$ group except —H and —OH. The crystal seed of the positive saponin nano micelle is most preferably one or more of ginsenoside Rg3, ginsenoside Rg5 and ginsenoside Rk1.

Wherein, the reverse saponin nano micelle can be the reverie saponin nano micelle prepared by the preparing methods mentioned above and/or any reverse saponin nano micelles mentioned above, preferably is Rg2/Rk4/Rg6-type reverse ginsenoside nano micelle.

Wherein, the organic solvent which can dissolve saponin can be the organic solvent that commonly used to dissolve ginsenoside and/or notoginsenoside in this field, preferably is selected from a group consisting of methanol, ethanol, N,N-dimethylformamide (DMF), n-butanol, propanol, tetrahydrofuran and pyridine.

Wherein, the methods and conditions of mixing can be the conventional methods and conditions in this field, and are subject to the uniformity of mixing. The mixing temperature preferably is 30° C.~80° C.

Wherein, the methods and conditions of removing organic solvent can be the conventional methods and conditions in this field. The way of removing organic solvent preferably is concentration and drying under reduced pressure at 30° C.~80° C. The way of removing organic solvent more preferably is: after the concentration and drying under reduced pressure, drying under vacuum at 30° C.~80° C. until the weight loss on drying is less than 3% mass percentage.

The present invention also provides a positive saponin nano micelle prepared by the preparing methods mentioned above.

The present invention also provides a use of the saponin nano micelle mentioned above as an aqueous solubilizer or a pharmaceutical carrier of lipid-soluble compound or composition, and the saponin nano micelle is positive saponin nano micelle.

Wherein, the lipid-soluble compound or composition can be the conventional lipid-soluble compound or composition in this field, preferably it selected from a group consisting of soy isoflavone, cardamonin, resveratrol, coenzyme Q10, vitamin A, vitamin D, vitamin E, vitamin K, Ginkgo biloba extract, melatonin, lycopene and β-carotene. The mass ratio of the lipid-soluble compounds or compositions and the saponin nano micelle preferably is (1:1)~(15:1), more preferably is 1:9.

In the present invention, the aqueous solubilizer means the solubilizer that can increase the solubility of water-indissolvable material in aqueous solution system.

The present invention also provides a use of the saponin nano micelle in preparing pharmaceutical preparations, health care products or cosmetics of water-indissolvable drug, the saponin nano micelle is positive saponin nano micelle.

Wherein, the water-indissolvable drug can be the conventional water-indissolvable drug in this field, preferably is selected from a group consisting of paclitaxel, docetaxel, cabazitaxel, irinotecan hydrochloride, topotecan hydrochloride, hydroxylcamptothecin, minoxidil, azithromycin, epirubicin hydrochloride, doxorubicin hydrochloride, doxorubicin hydrochloride ammonia, tacrolimus, fluoronacil, vincristine sulfate, vinblastine sulfate, vindesine sulfate, vinorelbine tartrate, huperzine A, homoharringtonine bases, three harringtonine, epothilone A, epothilone B, epothilone C, epothilone D, epothilone E, epothilone F, bortezomib, etoposide phosphate, hydrochloric acid, gemcitabine, fludarabine phosphate, fluvastatin, pravastatin, simvastatin, lovastatin, simvastatin, mevastatin, cerivastatin, rosuvastatin, atorvastatin calcium and rosuvastatin calcium. A mass ratio of the water-indissolvable drug and the saponin nano micelle preferably is (1:3)~(1:12), more preferably is 1:6.

The present invention also provides a pharmaceutical composition, which comprises the saponin nano micelle and the water-indissolvable drug; the saponin nano micelle is positive saponin nano micelle.

Wherein, a mass ratio of the water-indissolvable drug and the positive saponin nano micelle preferably is (1:3)~(1:12), more preferably is 1:6.

The present invention also provides a use of the saponin nano micelle as a lipidic solubilizer and a pharmaceutical carrier of water-soluble compound or composition, the saponin nano micelle is reverse saponin nano micelle.

Wherein, the water-soluble compound or composition can be the conventional water-soluble compound or composition in this field, preferably is selected from a group consisting of peptide, polypeptide, protein, nucleic acid (DNA or RNA (preferably RNAi) or fragments thereof), insulin, erythropoietin, leptin, growth factors, growth hormone-releasing hormone, colony stimulating factor, water-soluble hormone (parathyroid hormone or its fragments or analogs), luteinizing hormone releasing hormone (LHRH) and its analogs (such as nafarelin, buserelin, goserelin), interferon, cytokine, polysaccharide (such as heparin), heparin compound, DNA, RNA fragment and its plasmid, RNA interference as well as its immunity agent and vaccine agent. A mass ratio of the water-soluble compound or composition and the reverse saponin nano micelle preferably is (1:1)~(15:1), more preferably is 1:9.

In the present invention, the lipidic solubilizer means the solubilizer that can increase the solubility of lipid-indissolvable material in oil or lipid system.

The present invention also provides a pharmaceutical composition, which comprises the saponin nano micelle and the water-soluble compound or composition; the saponin nano micelle is reverse saponin nano micelle.

Wherein, the mass ratio of the water-soluble compound or composition and the reverse saponin nano micelle is preferably (1:1)~(15:1) more preferably is 1:9.

In the present invention, the mentioned optimized conditions can be optionally combined based on the general knowledge in this field to obtain preferred embodiments.

In the present invention, the used reagents and materials can be commercially available.

The positive effects of the present invention are:

1. The saponin nano micelle in the present invention is the first origination, wherein, the positive micelle can be used in lipid-soluble relevant ingredients in food, health care products and cosmetics, and make the relevant ingredients dissolve in water or alcohol to achieve nanocrystallization and play an important role in the application scope of product development; in addition, during actual use, the relevant ingredient is transported to action site, hydrolyzed under physiological conditions, released, and produce efficacy or effectiveness, while the ginsenoside and/or notoginsenoside also produce efficacy or play a helpful role.

2. The saponin nano micelle in the present invention is used as a drug carrier or applied to drugs, the positive micelle encapsulates the water-indissolvable drug active ingredients with stronger drug-loading capacity, higher biological compatibility, and at least 99.5% drug-loading rate, and the encapsulation ratio of which is still not less than 90% after the obtained drug-loading micelle left in glucose solution for more than 10 hours. As a convey medium of the drug ingredients, the positive micelle can replace conventional drug carriers such as pharmaceutical solubilizer or polymeric micelle, and overcomes the security problem of the existing solubilizer or polymer micelle, and is of great significance; the reverse micelle can be used as a solubilizer or preparation of water-soluble drugs or water-soluble ingredients, as well as drug-loading micelle of water-soluble drugs or ingredients.

DETAILED DESCRIPTION OF THE PREFERRED EMBODIMENT

Figure 1:
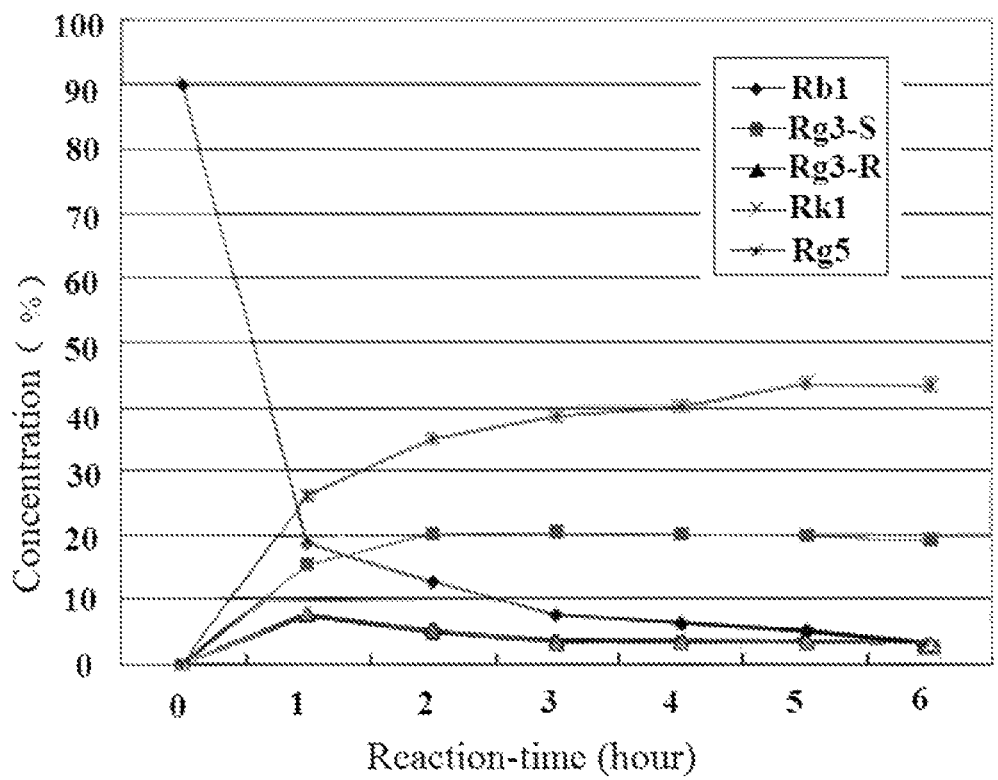
FIG. 1 is a figure of the concentration of each composition in reactant of the example 2 versus time.

Then the present invention is further illustrated by the following embodiments, but is not limited by the following embodiments. In the following embodiments, the experimental methods without specific conditions, can be carried on by conventional conditions or selected according to the commodity specification.

The ginsenoside compounds used in the following examples are commercially available, and also can be prepared according to the literature by the following methods:

The total ginsenoside is prepared according to the method of Chinese invention application patent CN200610093610.6, which uses roots, stems, leaves that selected from Chinese *ginseng* (*Panax ginseng*), Korean *ginseng* (*P. Sinensis J. Wen*), American *ginseng* (*P. quique folius*), Japanese *ginseng* (*P. japonicus*), Vietnamese *ginseng* (*P. vientnamensis*), Siberian *ginseng* (*Eleutherococcus senticosus*), *Panax* Pseudo-*ginseng* (*P. pseudoginseng*) and *Panax notoginseng* (*P. notoginseng*) and *gynostemma* as raw materials; and then the ginsenoside is divided into a mixed saponin A mainly comprising ginsenoside Re and ginsenoside Rg1 and a mixed saponin B mainly comprising ginsenoside F1, ginsenoside Rg2, ginsenoside F2, notoginsenoside Fe, ginsenoside Rd, ginsenoside Rb2, ginsenoside Rc, ginsenoside Rb1 and ginsenoside Rb3, by macroporous resin method (such as the method of Chinese invention application patent CN201010527369.X), then a ginsenoside mixture of more simple composition is obtained by a method of recrystallization or alumina column chromatography (such as the method in Chinese invention application patent CN200610093615.9), and finally ginsenoside monomer: ginsenoside Rb1, ginsenoside Rb2, ginsenoside Rb3, ginsenoside Rc, ginsenoside Rd, ginsenoside Rg1, ginsenoside Rg2, ginsenoside Rg3, ginsenoside Rh1, ginsenoside Rh2, ginsenoside Rh3, ginsenoside F1, ginsenoside F2 and notoginsenoside R1, is respectively obtained by column chromatography methods.

The preparing methods of ginsenoside monomers used in the following examples are as follows:

The monomer of ginsenoside Rb1, ginsenoside Rb3, ginsenoside Rd, ginsenoside Re and so on is prepared by an extract of American *ginseng* root:

the *ginseng* root 300 g with the mass content of 81% saponin, is dissolved in 4 L methanol, after ultrasonic assistance dissolution, 6 L water is added, a ginsenoside sample solution of 40 v/v % aqueous methanol solution is prepared.

10 L sample solution is pumped into preparative column (inner diameter 200 mm, height 2000 mm, the column filled with 10 μm-C18), the flow rate is 500 ml/min, mobile phase gradient elution is used that it first eluted by 40 v/v % aqueous methanol 200 L, eluted by 50 v/v % aqueous methanol 200 L, eluted by 60 v/v % aqueous methanol 400 L, eluted by 90 v/v % aqueous methanol 200 L, and Rb1 section, Rb3 section, Rd section, Re section, etc. is respectively obtained by fraction collecting according online UV monitoring. The collected fluid is respectively concentrated to below 1 L by nanofiltration membrane, and extracted for three times with n-butanol. The n-butanol is combined and concentrated to dryness, after drying, 28.5 g of 91.8% of ginsenoside Re, 6.8 g of 90.3% of ginsenoside Rb1, 3.6 g of 90.1% ginsenoside Rb3, and 36.0 g of 92.5% of ginsenoside Rd is obtained respectively.

According to the method mentioned above, by passing though column chromatographic repeatedly and preparing, 500 g of no less than 90% ginsenoside Re, 500 g of no less than 90% ginsenoside Rb1, 500 g of no less than 90% ginsenoside Rb3 and 500 g of no less than 90% ginsenoside Rd is obtained respectively.

Example 1

A preparing method for HSE-type ginsenoside nano micelle by total ginsenoside:

1). 100 g *ginseng* root with the mass content of 81% saponin is taken into reaction flask, 50 v/v % acetic acid solution 500 ml is added, it is hydrolyzed at 90° C. for 4 hours, after the reaction, the reaction flask is placed at room temperature for 12 hours, it is filtered by 0.4 μm filler paper to remove insolubles 9.1 g; the filtrate as neutralized with 2.4 L of 10 wt % Na$_2$CO$_3$, settled subsided, and filtered by 10 μm filter paper, and then a precipitate collected as obtained.

2). The precipitate is heated and dissolved at 60° C. in 1.0 L ethanol, placed at 4° C. for 2 hours, and filtered by 10 μm filter paper to remove sediment, the filtrate is concentrated under reduced pressure; then the concentrate by concentration under reduced pressure is dissolved in 0.4 L absolute ethanol, and then placed at 4° C. for 2 hours, filtered by 1.0 μm filter paper, and concentrated under reduced pressure to dryness, and 153 g HSE-type ginsenoside nano micelle is obtained by the preparation.

The analysis results of ingredients of the raw material used and the HSE-type ginsenoside nano micelle prepared in the example 1 by HPLC are shown in table 2.

HPLC analysis conditions are: column is ZORBAX Eclipse XDB-C18 4.6×250 mm; detection wavelength is UV/Vis, 203 mm; flow rate is 1.0 ml/min; column temperature is 50° C.; system running time is 80 min; mobile phase (gradient) is shown in the following table.

TABLE 1

| The changes of mobile phase (gradient) in HPLC | | | |
|---|---|---|---|
| Time (min) | flow rate (ml/min) | % purified water | % acetonitrile |
| 1 | 0 | 1.0 | 95 | 5 |
| 2 | 30 | 1.0 | 70 | 30 |
| 3 | 50 | 1.0 | 40 | 60 |
| 4 | 65 | 1.0 | 25 | 75 |
| 5 | 75 | 1.0 | 10 | 90 |
| 6 | 78 | 1.0 | 10 | 90 |
| 7 | 80 | 1.0 | 95 | 5 |

TABLE 2

The contents of ingredients of the raw material and the HSE-type ginsenoside nano micelle in the example 1

| Name of ginsenoside | Content of ginsenoside | HSE-type ginsenoside nano micelle |
|---|---|---|
| Re and Rg1 | 28.3% | 2.16% |
| Rf | 0.27% | — |
| Rh1 | — | — |
| Rg2 | — | — |
| Rb1 | 34.26% | 3.23% |
| Rc | 11.0% | 3.59% |
| Rb2 | 3.05% | 1.03% |
| F1 | — | — |
| Rd | 11.04% | — |
| Rg6 | 1.75% | 4.12% |
| F4 | 1.63% | 9.25% |
| Rk3 and F2 | 2.69% | 2.69% |
| Rh4 | 0.20% | 4.06% |
| Rg3-S | 1.55% | 11.01% |
| Rg3-R | 0.22% | 3.32% |
| PPT-S | — | — |
| F3 | — | — |
| RK4 | — | 3.21% |
| Ingredient K | — | — |
| RK1 | 1.05% | 14.95% |
| Rg5 | 0.46% | 30.93% |
| Rh2-S | — | 1.48% |
| Rh2-R | — | — |
| PPD-S | — | — |
| Total of other unknown impurities | 2.52% | 5.21% |
| Total | 100.0% | 100.0% |

Example 2

A preparing method for Rg3/Rg5/Rk1-type ginsenoside nano micelle from ginsenoside Rb1:

(1) 100 g ginsenoside Rb1 is taken into reaction vessel, 50 ml citric acid solution with pH 3.0 is added, 50 ml water is added and it is decomposed for 1~6 hours at 80° C.;

(2) The reaction solution obtained in the step (1) is placed in room temperature and cooled to 30° C., after neutralized by 10 wt % sodium carbonate, it is filtered by 10 μm filter paper, the sediment is removed, and the filtrate is obtained.

(3) The filtrate is extracted and separated for 2 times by 200 ml water and 100 n-butanol; and then 70 ml water is added into 200 ml n-butanol that obtained from extraction and separation, the n-butanol layer is concentrated under reduced pressure to obtain a solid, the solid is dissolved in 500 ml of ethanol and then refrigerated for 3 hours at 5° C., then filtered by 0.45 μm filter paper; the filtrate is concentrated under reduced pressure and pulverized to obtain 33 g Rg3/Rg5/Rk1-type ginsenoside nano micelle.

In the preparation process of the example, the ingredients of the reaction solution are detected and analyzed by HPLC under the same conditions as in the example 1, table 3 and FIG. 1 show the mass content of the ingredients in reaction solution with the change of time, under the condition, the ginsenoside nano micelle composition is prepared as shown in table 3, ginsenoside Rb1 becomes less with the increasing of reaction time, and eventually Rg3/Rg5/Rk1-type ginsenoside nano micelle with the mass ratio of Rg3:Rk1:Rg5=(1:1:2) is obtained.

TABLE 3

The relationship of each ingredient in reactant over time in the example 2

| Reaction time | Rb1 | Rg3-S | Rg3-R | Rk1 | Rg5 | Other unknown impurities |
|---|---|---|---|---|---|---|
| Rb1 | 90.0% | — | — | — | — | 10.0% |
| 1 hour | 18.7% | 15.5% | 7.7% | 18.3% | 26.3% | / |
| 2 hour | 12.7% | 20.2% | 5.2% | 24.6% | 35.0% | / |
| 3 hour | 7.5% | 20.7% | 3.5% | 26.7% | 38.7% | / |
| 4 hour | 6.3% | 20.1% | 3.5% | 24.5% | 40.1% | / |
| 5 hour | 5.1% | 19.9% | 3.4% | 23.8% | 43.6% | / |
| 6 hour | 2.7% | 19.4% | 3.2% | 23.9% | 43.3% | / |

The prepared Rg3/Rg5/Rk1-type ginsenoside nano micelle in the present example can replace the existing Cremophor EL or Tween 80.

Example 3

A preparing method for Rg3/Rg5/Rk1-type ginsenoside nano micelle from Rb3 ginsenoside micelle:

100 g ginsenoside Rb3 is taken into reaction vessel, the preparing method is the same as the method in the example 2, and 38 g Rg3/Rg5/Rk1-type ginsenoside nano micelle is obtained. The ingredients are detected and analyzed by HPLC as same as in the example 1, and the result is shown in table 4.

TABLE 4

The content of ingredients of raw material ginsenoside Rb3 and ginsenoside nano micelle in the example 3

| ginsenoside | raw material ginsenoside Rb3 | Rg3/Rg5/Rk1-type ginsenoside nano micelle |
|---|---|---|
| Rb3 | 90.1% | 3.6% |
| Rg3-S | — | 19.8% |
| Rg3-R | — | 2.7% |
| Rg-5 | — | 43.3% |
| Rk1 | — | 21.6% |
| Total of other unknown impurities | 9.9% | 9.0% |
| Total | 100.0% | 100.0% |

Example 4

A preparing method for Rg3/Rg5/Rk1-type ginsenoside nano micelle from ginsenoside Rd:

100 g ginsenoside Rd is taken into reaction vessel, the preparing method is the same as the method in the example 2, and 23 g Rg3/Rg5/Rk1-type ginsenoside nano micelle is obtained. The ingredients are detected and analyzed by HPLC as same as in the example 1, and the result is shown in table 5.

TABLE 5

The content of ingredients of raw material ginsenoside Rd and ginsenoside nano micelle in the example 4.

| ginsenoside | raw material ginsenoside Rd | Rg3/Rg5/Rk1-type ginsenoside nano micelle |
|---|---|---|
| Rd | 92.5% | 4.1% |
| Rg3-S | — | 18.6% |
| Rg3-R | — | 3.5% |

TABLE 5-continued

The content of ingredients of raw material ginsenoside Rd and ginsenoside nano micelle in the example 4.

| ginsenoside | raw material ginsenoside Rd | Rg3/Rg5/Rk1-type ginsenoside nano micelle |
|---|---|---|
| Rg-5 | — | 39.4% |
| Rk1 | — | 21.4% |
| Total of other unknown impurities | 7.5% | 13.0% |
| Total | 100.0% | 100.0% |

Example 5

A preparing method for Rg2/Rk4/Rg6-type reverse ginsenoside nano micelle from ginsenoside Re:

100 g ginsenoside Re is taken into reaction vessel, the preparing method is the same as the method in the example 2, and 30 g Rg2/Rk4/Rg6-type reverse ginsenoside nano micelle is obtained. The ingredients are detected and analyzed by HPLC as same as in the example 1, and the result is shown in table 6.

TABLE 6

The content of ingredients of raw material ginsenoside Re and reverse ginsenoside nano micelle in the example 5.

| ginsenoside | raw material ginsenoside Re | Rg2/Rg4/Rk6-type reverse ginsenoside nano micelle |
|---|---|---|
| Re | 91.4% | 1.5% |
| Rg2 | — | 22.2% |
| Rg4 | — | 39.3% |
| Rg6 | — | 20.9% |
| Total of other unknown impurities | 8.6% | 16.1% |
| Total | 100.0% | 100.0% |

Example 6

A preparing method for Rg2/Rk4/Rg6-type positive ginsenoside nano micelle from ginsenoside Re:

100 g ginsenoside Re is taken into reaction vessel, the preparing method is the same as the method in the example 5, and 30 g Rg2/Rk4 Rg6-type ginsenoside reverse micelle is obtained.

10 g of Rg2/Rk4/Rg6-type ginsenoside nano reverse micelle is taken and dissolved in 200 ml absolute ethanol, concentrated to 100 ml under reduced vacuum, and a little amount crystal seed of Rg3/Rg5/Rk1 micelle is added, it is cooled and crystallized and then filtrated to dryness, and 5.4 g Rg2/Rk4/Rg6-type positive ginsenoside nano micelle is obtained.

The raw material ginsenoside Re used in the example and the Rg2/Rk4/Rg6-type positive ginsenoside nano micelle prepared in the example are detected and analyzed by HPLC as same as in the example 1, the result is shown in table 7.

TABLE 7

The content of ingredients of raw material ginsenoside Re and ginsenoside nano micelle in the example 6

| ginsenoside | raw material ginsenoside Re | Rg2/Rg4/Rk6-type positive ginsenoside nano micelle |
|---|---|---|
| Re | 91.4% | 1.6% |
| Rg2 | — | 22.4% |
| Rg4 | — | 39.5% |
| Rg6 | — | 21.1% |
| Total of other unknown impurities | 8.6% | 15.4% |
| Total | 100.0% | 100.0% |

Example 7

A preparing method for Rh2-type ginsenoside nano micelle from ginsenoside F2:

100 g ginsenoside F2 is taken, the preparing method is the same as the method in example 1, and 16 g Rh2-type ginsenoside micelle is obtained.

The ginsenoside F2 is prepared by the following method:

200 g ginsenoside Rb1 with high purity is taken into reaction vessel, 500 ml of purified water is added, and alpha-galactosidase is added, it is decomposed by enzymolysis at 30° C. for 4~44 hours (more preferably 8~12 hours, extracted with 200 ml n-butanol for three times, and the n-butanol is combined, concentrated under reduced pressure and dried to obtain 136 g ginsenoside F2.

The raw material ginsenoside Rb1 used in the example, the ginsenoside F2 and the Rh2-type nano micelle prepared in the present example are detected and analyzed by HPLC as same as in the example 1, and the result is shown in table 8.

TABLE 8

The content of ingredients of raw material ginsenoside Rb1, ginsenoside F2 and ginsenoside nano micelle in the example 7

| ginsenoside | raw material ginsenoside Rb1 | ginsenoside F2 | Rg2-type ginsenoside nano micelle |
|---|---|---|---|
| Rb1 | 90.0% | 0.6% | -% |
| F2 | — | 86.4% | 1.6% |
| Rh2 | — | — | 21.3% |
| Rh3 | — | — | 38.8% |
| Rk2 | — | — | 20.2% |
| Total of other unknown impurities | 10.0% | 13% | 18.1% |
| Total | 100.0% | 100.0% | 100.0% |

Example 8

A preparing method for Rg5/Rk1-type ginsenoside micelle from Rg3/Rg5/Rk1-type ginsenoside nano micelle as raw material:

100 g raw material Rg3/Rg5/Rk1-type ginsenoside nano micelle is taken, separated by the same aforementioned method of preparing the ginsenoside monomers, after column chromatography separation, fragmentation, nanofiltration membrane concentration, extraction by n-butanol, concentration under reduce pressure and dryness, 36 g mixture of Rg5:Rk1=1:1 is obtained. Then the 36 g mixture is dissolved in 200 ml absolute ethanol, and then concentrated under reduced pressure to dryness to obtain 36 g Rg5/Rk1-type ginsenoside nano micelle. The ingredients are detected and analyzed by HPLC as same as in the example 1, and the result is shown in table 9.

TABLE 9

The content of ingredients of Rg5/Rk1-type ginsenoside nano micelle in the example 8

| ginsenoside | raw material Rg3/Rg5/Rk1-type ginsenoside nano micelle | Rg5/Rk1-type ginsenoside nano micelle |
|---|---|---|
| Rb3 | 3.6% | — |
| Rg3-S | 19.8% | 0.1% |
| Rg3-R | 2.7% | — |
| Rg5 | 43.3% | 45.6% |
| Rk1 | 21.6% | 44.8% |
| Total of other unknown impurities | 9.0% | 9.5% |
| Total | 100.0% | 100.0% |

Example 9

A preparing method for Rg5-type ginsenoside nano micelle from Rg3/Rg5/Rk1-type ginsenoside micelle as raw material.

The preparing method is the same as the method in the example 8, the enrichment section of Rg5 is taken, concentrated by nanofiltration membrane, extracted by n-butanol, concentrated under reduced pressure, dried and then 8.5 g Rg5 monomer is obtained. The 8.5 g Rg5 monomer is dissolved in 50 ml absolute ethanol, and then concentrated under reduced pressure to dryness to obtain 8.6 g Rg5-type ginsenoside nano micelle. The ingredients are detected and analyzed by HPLC as same as in the example 1, and the result is shown in table 10.

TABLE 10

The content of ingredients of Rg5-type ginsenoside nano micelle in the example 9

| ginsenoside | raw material Rg3/Rg5/Rk1-type ginsenoside nano micelle | Rg5-type ginsenoside nano micelle |
|---|---|---|
| Rb3 | 3.6% | — |
| Rg3-S | 19.8% | 1.4% |
| Rg3-R | 2.7% | 0.1% |
| Rg5 | 43.3% | 92.6% |
| Rk1 | 21.6% | 2.1% |
| Total of other unknown impurities | 9.0% | 3.8% |
| Total | 100.0% | 100.0% |

Example 10

A preparing method for Rk1-type ginsenoside nano micelle from Rg3/Rg5/Rk1-type ginsenoside micelle as raw material:

The preparing method is the same as the method in the example 8, the enrichment section of Rk1 is taken, concentrated by nanofiltration membrane, extracted by n-butanol, concentrated under reduced pressure, dried and then 2.6 g Rk1 monomer is obtained. The 2.6 g Rk1 monomer is dissolved in 20 ml absolute ethanol, and then concentrated under reduced pressure to dryness to obtain 2.6 g Rk1-type ginsenoside nano micelle. The ingredients are detected and analyzed by HPLC as same as in the example 1, and the result is shown in table 11.

TABLE 11

The content of ingredients of Rk1-type ginsenoside nano micelle in the example 10

| ginsenoside | raw material Rg3/Rg5/Rk1-type ginsenoside nano micelle | Rk1-type ginsenoside nano micelle |
|---|---|---|
| Rb3 | 3.6% | — |
| Rg3-S | 19.8% | — |
| Rg3-R | 2.7% | — |
| Rg5 | 43.3% | 5.6% |
| Rk1 | 21.6% | 90.1% |
| Total of other unknown impurities | 9.0% | 4.3% |
| Total | 100.0% | 100.0% |

Example 11

A preparing method for Rk4/Rg6-type reverse ginsenoside nano micelle from Rg2/Rk4/Rg6-type ginsenoside micelle as raw material:

100 g Rg2/Rk4/Rg6-type ginsenoside nano micelle is taken, separated by the same aforementioned the preparing method for the ginsenoside monomers, after column chromatography separation, fragmentation, nanofiltration membrane concentration, n-butanol extraction, concentration under reduce pressure and drying, and 27 g mixture of Rk4:Rg6=1:1 is obtained. Then the 27 g mixture is dissolved in 200 ml absolute ethanol, and then concentrated under reduced pressure to dryness to obtain 27 g Rk4/Rg6-type reverse ginsenoside nano micelle. The ingredients are detected and analyzed by HPLC as same as in the example 1, and the result is shown in table 12.

TABLE 12

The content of ingredients of Rk4/Rg6-type reverse ginsenoside nano micelle in the example 11

| ginsenoside | raw material Rg2/Rk4/Rg6-type ginsenoside micelle | Rk4/Rg6-type ginsenoside reverse micelle |
|---|---|---|
| Re | 1.5% | — |
| Rg2 | 22.2% | 3.5% |
| Rk4 | 39.3% | 42.8% |
| Rg6 | 20.9% | 43.6% |
| Total of other unknown impurities | 16.1% | 10.1% |
| Total | 100.0% | 100.0% |

Example 12

A preparing method for Rk4-type reverse ginsenoside nano micelle from Rg2/Rk4/Rg6-type ginsenoside micelle as raw material:

The preparing method is the same as the method in the example 11, the enrichment section of Rk4 is taken, concentrated by nano filtration membrane, extracted by n-butanol, concentrated under reduced pressure, dried and 3.3 g Rk4 monomer is obtained. The 3.3 g mixture is dissolved in 20 ml absolute ethanol, and then concentrated under reduced pressure to dryness to obtain 3.3 g Rk4-type reverse ginsenoside nano micelle. The ingredients are detected and analyzed by HPLC as same as in the example 1, and the result is shown in table 13.

TABLE 13

The content of ingredients of Rk4-type reverse ginsenoside nano micelle in the example 12

| ginsenoside | raw material Rg2/Rk4/Rg6-type ginsenoside nano micelle | Rk4-type ginsenoside nano micelle |
|---|---|---|
| Re | 1.5% | — |
| Rg2 | 22.2% | 2.1% |
| Rk4 | 39.3% | 91.7% |
| Rg6 | 20.9% | 5.9% |
| Total of other unknown impurities | 16.1% | 0.3% |
| Total | 100.0% | 100.0% |

Example 13

A preparing method for Rg6-type reverse ginsenoside nano micelle from Rg2/Rk4/Rg6-type ginsenoside micelle as raw material:

The preparing method is the same as the method in the example 11, the enrichment section of Rg6 is taken, concentrated by nanofiltration membrane, extracted by n-butanol, concentrated under reduced pressure, dried and 3.0 g Rg6 monomer is obtained. The 3.0 mixture is dissolved in 20 ml absolute ethanol, and then concentrated under reduced pressure to dryness to obtain 3.0 g Rg6-type reverse ginsenoside nano micelle. The ingredients are detected and analyzed by HPLC as same as in the example 1, and the result is shown in table 14.

TABLE 14

The content of ingredients of Rk6-type reverse ginsenoside nano micelle in the example 13

| ginsenoside | raw material Rg2/Rk4/Rg6-type ginsenoside nano micelle | Rg6-type ginsenoside reverse micelle |
|---|---|---|
| Re | 1.5% | — |
| Rg2 | 22.2% | 0.5% |
| Rk4 | 39.3% | 8.3% |
| Rg6 | 20.9% | 88.1% |
| Total of other unknown impurities | 16.1% | 3.1% |
| Total | 100.0% | 100.0% |

Examples 14~43

Each content of ingredients in examples 14 to 43 is shown in tables 15~18, each ingredient is dissolved in ethanol, then the organic solvent is removed, and the ginsenoside micelle is obtained.

TABLE 15

The ingredients and dosages of examples 14~19

| Number of example | ingredients and dosages (weight percentage,%) | | | |
|---|---|---|---|---|
| | ginsenoside Rg3 | ginsenoside Rg5 | ginsenoside Rk1 | Other types of ginsenoside impurities |
| 14 | 15 | 45 | 35 | 5 |
| 15 | 15 | 15 | 45 | 25 |
| 16 | 45 | 15 | 15 | 25 |
| 17 | 25 | 35 | 20 | 20 |
| 18 | 25 | 35 | 25 | 15 |
| 19 | 20 | 40 | 20 | 20 |

TABLE 16

The ingredients and dosages of examples 20~25

| Number of example | ingredients and dosages (weight percentage,%) | | | |
|---|---|---|---|---|
| | ginsenoside Rh2 | ginsenoside Rh3 | ginsenoside Rk2 | Other types of ginsenoside impurities |
| 20 | 15 | 45 | 35 | 5 |
| 21 | 15 | 15 | 45 | 25 |
| 22 | 45 | 15 | 15 | 25 |
| 13 | 25 | 35 | 20 | 20 |
| 24 | 25 | 35 | 25 | 15 |
| 25 | 20 | 40 | 20 | 20 |

TABLE 17

The ingredients and dosage of examples 26~31

| Number of example | ingredients and dosages (weight percentage,%) | | | |
|---|---|---|---|---|
| | ginsenoside Rg2 | ginsenoside Rk4 | ginsenoside Rg6 | Other types of ginsenoside impurities |
| 26 | 15 | 45 | 35 | 5 |
| 27 | 15 | 15 | 45 | 25 |
| 28 | 45 | 15 | 15 | 25 |
| 29 | 25 | 35 | 20 | 20 |
| 30 | 25 | 35 | 25 | 15 |
| 31 | 20 | 40 | 20 | 20 |

TABLE 18

The ingredients and dosages of examples 32-43 ingredients and dosages (weight percentage, %)

| No. | ginsenoside Rg2 | ginsenoside Rg3 | ginsenoside Rh1 | ginsenoside Rg5 | ginsenoside Rk4 | ginsenoside Rh4 | ginsenoside Rk1 | ginsenoside Rg6 | ginsenoside Rk3 | Other types of ginsenoside impurities |
|---|---|---|---|---|---|---|---|---|---|---|
| 32 | 4 | 5 | 6 | 16 | 15 | 14 | 6 | 4 | 5 | 25 |
| 33 | 5 | 5 | 5 | 14 | 15 | 16 | 3 | 5 | 7 | 25 |

TABLE 18-continued

The ingredients and dosages of examples 32-43 ingredients and dosages (weight percentage, %)

| No. | ginseno-side Rg2 | ginseno-side Rg3 | ginseno-side Rh1 | ginseno-side Rg5 | ginseno-side Rk4 | ginseno-side Rh4 | ginseno-side Rk1 | ginseno-side Rg6 | ginseno-side Rk3 | Other types of ginseno-side impurities |
|---|---|---|---|---|---|---|---|---|---|---|
| 34 | 3  | 5  | 7  | 15 | 14 | 16 | 4 | 5  | 6  | 25 |
| 35 | 16 | 15 | 14 | 4  | 5  | 6  | 6 | 4  | 5  | 25 |
| 36 | 14 | 15 | 16 | 5  | 5  | 5  | 3 | 5  | 7  | 25 |
| 37 | 15 | 14 | 16 | 3  | 5  | 7  | 4 | 5  | 6  | 25 |
| 38 | 6  | 4  | 5  | 16 | 15 | 14 | 4 | 5  | 6  | 25 |
| 39 | 3  | 5  | 7  | 14 | 15 | 16 | 5 | 5  | 5  | 25 |
| 40 | 4  | 5  | 6  | 15 | 14 | 16 | 3 | 5  | 7  | 25 |
| 41 | 5  | 10 | 10 | 5  | 15 | 15 | 5 | 13 | 17 | 5  |
| 42 | 5  | 15 | 15 | 5  | 13 | 17 | 5 | 10 | 10 | 5  |
| 43 | 5  | 13 | 7  | 5  | 10 | 10 | 8 | 12 | 10 | 20 |

Application Example 1

Figure 2:
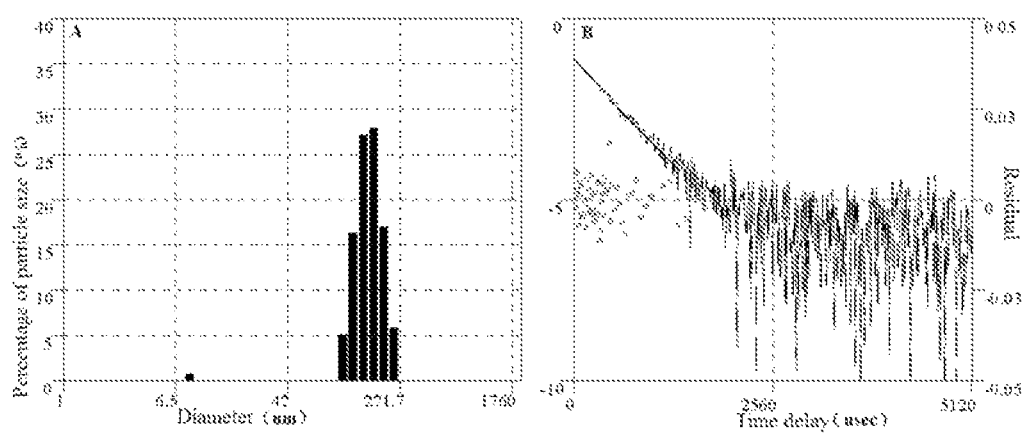
FIG. 2 is a size distribution figure of the drug-loading ginsenoside nano micelle in the application example 1.

The drug-loading formulation of paclitaxel and Rg3/Rg5/Rk1-type micelle:

30 mg paclitaxel and 180 mg Rg3/Rg5/Rk1-type ginsenoside nano micelle in the example 2 are added to 5 ml small bottle, and 2.0 ml absolute ethanol is added, then they are dissolved by vortex mixer and then filtered by 0.45 μm filter paper, then a solution dissolving paclitaxel encapsulated by micelle has been prepared. The particle size distribution is detected, and the result is shown in FIG. 2.

Figure 3:
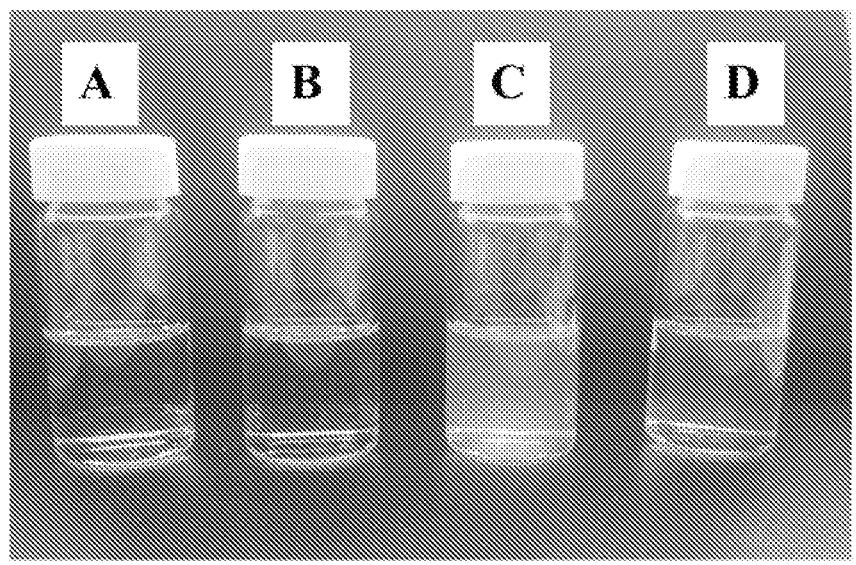
FIG. 3 is an imaging figure of the drug-loading micelle solution and its comparison in the application examples 1~2.

The solution dissolving paclitaxel encapsulated by micelle mentioned above is added into 75 ml commercially available glucose injection solution, the imaging figure after being settled at room temperature for 12 hours is shown in FIG. 3B; as a contrast, 30 mg paclitaxel injection that is commercially available from Beijing Union Pharmaceutical Factory is added into 75 ml commercially available glucose injection solution and settled at room temperature for 12 hours, and the produced imaging figure is shown in FIG. 3D; it is apparent that paclitaxel micelle solution is clear and transparent. By test, the drug-loading rate or ginsenoside nano micelle is at least 99.5% and after the obtained drug-loading micelle placed in glucose solution for at least 10 hours, the encapsulation efficiency is still no less than 90%.

In addition to the above, the solutions dissolving paclitaxel encapsulated by micelle are also prepared, in which the mass of drugs and ginsenoside micelle is the following combinations: 10 mg and 30 mg, 10 mg and 120 mg or 10 mg and 60 mg.

Application Example 2

The drug-loading formulation of paclitaxel and Rg5/Rk1-type micelle:

30 mg paclitaxel and 180 mg Rg5/Rk1-type ginsenoside nano micelle in the example 8 are added to 5 ml small bottle and 2.0 ml absolute ethanol is added, then they are dissolved by vortex mixer and then filtered by 0.45 μm filter paper, then a solution dissolving paclitaxel encapsulated by micelle has been prepared.

The solution dissolving paclitaxel encapsulated by micelle mentioned above is added into 75 ml commercially available glucose injection solution, then settled at room temperature for 12 hours; as a contrast, 30 mg paclitaxel injection that is commercially available from Beijing Union Pharmaceutical Factory is added into 75 ml commercially available glucose solution, then settled at room temperature for 12 hours; it is apparent that paclitaxel micelle solution is clear and transparent, while the contrast sample is murky. By test, the drug-loading rate of ginsenoside nano micelle is at least 99.5% and after the obtained drug-loading micelle placed in glucose solution for at least 10 hours, the encapsulation efficiency is still no less than 90%.

In addition to the above, the solutions dissolving paclitaxel encapsulated by micelle are prepared, in which the mass of drugs and ginsenoside micelle is the following combinations: 10 mg and 30 mg, 10 mg and 120 mg or 10 mg and 60 mg.

Application Example 3

The drug-loading formulation of paclitaxel and Rg5-type micelle:

30 mg paclitaxel and 180 mg Rg5-type ginsenoside nano micelle in the example 9 are added to 5 ml small bottle and 2.0 ml absolute ethanol is added, then they are dissolved by vortex mixer and then filtered by 0.45 μm filter paper, then a solution dissolving paclitaxel encapsulated by micelle has been prepared.

The solution dissolving paclitaxel encapsulated by micelle mentioned above is added into 75 ml commercially available glucose injection solution, then settled at room temperature for 12 hours; as a contrast, 30 mg paclitaxel injection that is commercially available from Beijing Union Pharmaceutical Factory is added into 75 ml commercially available glucose solution, settled at room temperature for 12 hours; it is apparent that paclitaxel micelle solution is clear and transparent, while the contrast sample is murky. By test, the drug-loading rate of ginsenoside nano micelle is at least 99.5% and after the obtained drug-loading micelle placed in glucose solution for at least 10 hours, the encapsulation efficiency is still no less than 90%.

In addition to the above, the solutions dissolving paclitaxel encapsulated by micelle are prepared, in which the mass of drugs and ginsenoside micelle is the following combinations: 10 mg and 30 mg, 10 mg and 120 mg or 10 mg and 60 mg.

Application Example 4

The drug-loading formulation of paclitaxel and Rh2-type micelle:

30 mg paclitaxel and 180 mg Rh2-type ginsenoside nano micelle in the example 7 are added to 5 ml small bottle and 2.0 ml absolute ethanol is added, then they are dissolved by vortex mixer and then filtered by 0.45 μm filter paper, then a solution dissolving paclitaxel encapsulated by micelle has been prepared.

The solution dissolving paclitaxel encapsulated by micelle mentioned above is added into 75 ml commercially available glucose injection solution, then settled at room temperature for 12 hours; as a contrast, 30 mg paclitaxel injection that is commercially available from Beijing Union Pharmaceutical Factory is added into 75 ml commercially available glucose solution, settled at room temperature for 12 hours; it is apparent that paclitaxel micelle solution is clear and transparent, while the contrast sample is murky. By test, the drug-loading rate of ginsenoside nano micelle is at least 99.5% and after the obtained drug-loading micelle placed in glucose solution for at least 10 hours, the encapsulation efficiency is still no less than 90%.

In addition to the above, the solutions dissolving paclitaxel encapsulated by micelle are prepared, in which the mass of drugs and ginsenoside micelle is the following combinations: 10 mg and 30 mg, 10 mg and 120 mg or 10 mg and 60 mg.

Application Example 5

The drug-loading formulation of paclitaxel and Rg2/Rk4/Rg6-type micelle:

30 mg paclitaxel and 180 mg Rg2/Rk4/Rg6-type ginsenoside nano micelle in the example 6 are added to 5 ml small bottle and 2.0 ml absolute ethanol is added, then they are dissolved by vortex mixer and then filtered by 0.4 μm filler paper, then a solution dissolving paclitaxel encapsulated by micelle has been prepared.

The solution dissolving paclitaxel encapsulated by micelle mentioned above is added into 75 ml commercially available glucose injection solution, then settled at room temperature for 12 hours; as a contrast, 30 mg paclitaxel injection that is commercially available from Beijing Union Pharmaceutical Factory is added into 75 ml commercially available glucose solution, settled at room temperature for 12 hours; it is apparent that paclitaxel micelle solution is clear and transparent, while the contrast sample is murky. By test, the drug-loading rate of ginsenoside nano micelle is at least 99.5% and after the obtained drug-loading micelle placed in glucose solution for at least 10 hours, the encapsulation efficiency is still no less than 90%.

In addition to the above, the solutions dissolving paclitaxel encapsulated by micelle are prepared, in which the mass of drugs and ginsenoside micelle is the following combinations: 10 mg and 30 mg, 10 mg and 120 mg or 10 mg and 60 mg.

Application Example 6

The drug-loading formulation of docetaxel anhydrous and Rg5/Rk1-type micelle:

30 mg docetaxel anhydrous and 180 mg Rg5/Rk1-type ginsenoside nano micelle in the example 8 are added to 5 ml small bottle and 20 ml absolute ethanol is added, then they are dissolved by vortex mixer and then filtered by 0.45 μm filter paper, then a solution dissolving docetaxel anhydrous encapsulated by micelle has been prepared.

The solution dissolving docetaxel anhydrous encapsulated by micelle mentioned above is added into 75 ml commercially available glucose solution for injection, then settled at room temperature for 12 hours; as a contrast, 30 mg paclitaxel injection that is commercially available from Shandong Qilu Pharmaceutical Factory is added into 75 ml commercially available glucose injection solution, then settled at room temperature for 12 hours; it is apparent that paclitaxel micelle solution is clear and transparent, while the contrast sample is murky. By test, the drug-loading rate of ginsenoside nano micelle is at least 99.5% and after the obtained drug-loading micelle placed in glucose solution for at least 10 hours, the encapsulation efficiency is still no less than 90%.

In addition to the above, the solutions dissolving docetaxel anhydrous encapsulated by micelle are prepared, in which the mass of drugs and ginsenoside micelle is the following combinations: 10 mg and 30 mg, 10 mg and 120 mg or 10 mg and 60 mg.

Application Example 7

Figure 4:
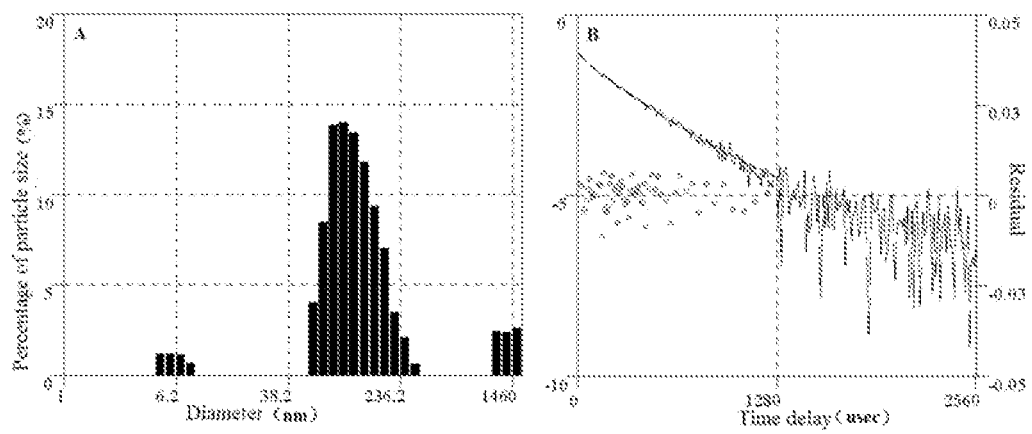
FIG. 4 is a size distribution figure of drug-loading ginsenoside nano micelle in the application example 7.

The drug-loading formulation of docetaxel anhydrous and Rg3/Rg5/Rk1-type micelle:

20 mg docetaxel anhydrous and 120 mg Rg3/Rg5/Rk1-type ginsenoside nano micelle in the example 2 are added to a 5 ml bottle and 2.0 ml absolute ethanol is added, then they are dissolved by vortex mixer and then filtered by 0.45 μm filter paper, then it solution dissolving docetaxel anhydrous encapsulated by micelle has been prepared. The particle size distribution is detected, and the result is shown in FIG. 4.

the solution dissolving docetaxel anhydrous encapsulated by micelle mentioned above is added into 75 ml commercially available glucose injection solution, then settled at room temperature for 12 hours, and the imaging figure is shown in FIG. 3A; as a contrast, 20 mg docetaxel injection that is commercially available from Jiangsu Hengrui Pharmaceutical co. LTD, is added into 75 ml commercially available glucose injection solution, then settled at room temperature for 12 hours, and the imaging figure is shown in FIG. 3C; it is apparent that paclitaxel micelle solution is clear and transparent, while the contrast sample is murky. By test, the drug-loading rate of ginsenoside nano micelle is at least 99.5% and after the obtained drug-loading micelle obtained placed in glucose solution for at least 10 hours, the encapsulation efficiency is still no less than 90%.

In addition to the above, the solutions dissolving docetaxel anhydrous encapsulated by micelle are prepared, in which the mass of drugs and ginsenoside micelle is the following combinations: 10 mg and 30 mg, 10 mg and 120 mg or 10 mg and 60 mg.

Application Example 8

Figure 5:
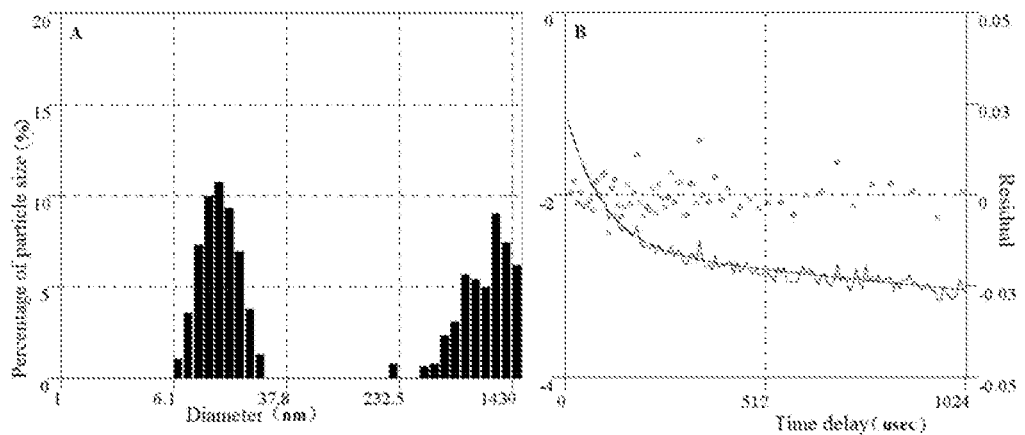
FIG. 5 is a size distribution figure of drug-loading ginsenoside nano micelle in the application example 8.

The drug-loading formulation of docetaxel trihydrate and Rh2-type micelle:

20 mg Docetaxel trihydrate and 120 mg Rh2-type ginsenoside nano micelle in the example 7 are added to a 5 ml bottle and 2.0 ml absolute ethanol is added, then they are dissolved by vortex mixer and then filtered by 0.45 μm filter paper, then a solution dissolving docetaxel trihydrate encapsulated by micelle has been prepared. The particle size distribution is detected, and the result is shown in FIG. 5. By test, the drug-loading rate of ginsenoside nano micelle is at least 99.5% and after the obtained drug-loading micelle placed in glucose solution for at least 10 hours, the encapsulation efficiency is still no less than 90%.

In addition to the above, the solutions dissolving docetaxel trihydrate encapsulated by micelle are prepared, in which the mass of drugs and ginsenoside micelle is the following combinations: 10 mg and 30 mg, 10 mg and 120 mg or 10 mg and 60 mg.

Application Example 9

The drug-loading formulation of minoxidil and HSE-type micelle:

20 mg Minoxidil and 120 mg HSE-type ginsenoside nano micelle in the example 1 are added to a 5 ml bottle and 2.0 ml absolute ethanol is added, then they are dissolved by vortex mixer and then filtered by 0.45 μm filter paper, then a solution dissolving minoxidil encapsulated by micelle has been prepared. The particle size distribution is detected, and the result is shown in FIG. 5. By test, the drug-loading rate of ginsenoside nano micelle is at least 99.5% and after the obtained drug-loading micelle placed in glucose solution for at least 10 hours, the encapsulation efficiency is still no less than 90%.

In addition to the above, the solutions dissolving minoxidil encapsulated by micelle are prepared, in which the mass of drugs and ginsenoside micelle is the following combinations: 10 mg and 30 mg, 10 mg and 120 mg or 10 mg and 60 mg.

Application Example 10

The drug-loading formulation of isoflavone and HSE-type micelle:

1.0 g Isoflavone (40%) and 9.0 g HSE-type ginsenoside nano micelle in the example 1 are added to a 50 ml beaker and 10 ml absolute ethanol is added, then they are dissolved by vortex mixer and then filtered by a 0.45 μm filter paper concentrated under reduced pressure and dried, then a nano micelle encapsulating isoflavone has been prepared. By test, the drug-loading rate of ginsenoside nano micelle is at least 99.5% and after the obtained drug-loading micelle placed in glucose solution for at least 10 hours, the encapsulation efficiency is still no less than 90%.

In addition to the above, the nano micelles encapsulating isoflavone are prepared, in which the mass of drugs and ginsenoside micelle as the following combinations: 10 mg and 10 mg, 10 mg and 120 mg or 10 mg and 90 mg.

Application Example 11

The drug-loading formulation of cardamonin and HSE-type micelle:

Cardamonin, a indissolvable ingredient in cosmetics 1.0 g. is added to a 50 ml bottle with 9.0 g HSE-type ginsenoside nano micelle in the example 1, and 10 ml absolute ethanol is added, then they are dissolved by the vortex mixer and then filtered by 0.45 μm filter paper, concentrated under reduced pressure and dried, then a nano micelle encapsulating cardamonin has been prepared. By test, the drug-loading rate of ginsenoside nano micelle is at least 99.5% and after the obtained drug-loading micelle placed in glucose solution for at least 10 hours, the encapsulation efficiency is still no less than 90%.

In addition to the above, the nano micelles encapsulating cardamonin are prepared, in which the mass of drugs and ginsenoside micelle is the following combinations: 10 mg and 10 mg, 10 mg and 120 mg or 10 mg and 90 mg.

Application Example 12

The drug-loading formulation of resveratrol and Rg2/Rk4/Rg6-type positive micelle:

1.0 g resveratrol and 9.0 g Rg2/Rk4/Rg6-type positive ginsenoside nano micelle in the example 6 are added to a 50 ml bottle and 10 ml absolute ethanol is added, then they are dissolved by the vortex mixer and then filtered by 0.45 μm filter paper to obtain a filtrate, the filtrate is concentrated under reduced pressure and dried, then a nano micelle encapsulating resveratrol has been prepared.

Figure 6:
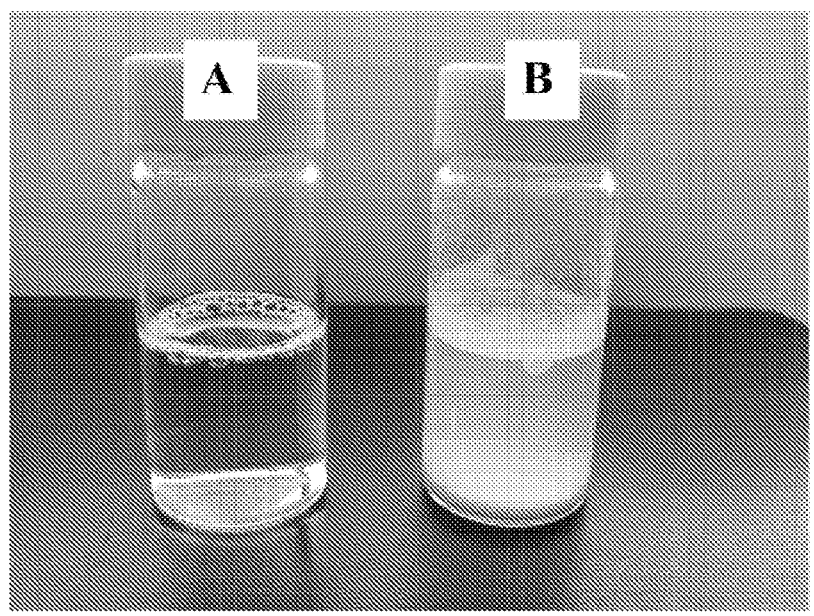
FIG. 6 is an imaging figure of the resveratrol drug-loading micelle solution and its comparison in the application example 12.

Wherein, the imaging figure of the filtrate mentioned above is shown in FIG. 6A, and as a contrast, 1.0 g resveratrol is added into a 50 ml bottle and 10 ml absolute ethanol is added, after it dissolved, the obtained imaging figure is shown in FIG. 6B; it is apparent that the resveratrol drug-loading micelle solution is clear and transparent, while the contrast sample is murky. By test, the drug-loading rate of ginsenoside nano micelle is at least 99.5% and after the obtained drug-loading micelle placed in glucose solution for at least 10 hours, the encapsulation efficiency is still no less than 90%.

In addition to the above, the nano micelles encapsulating resveratrol are prepared, in which the mass of drugs and ginsenoside micelle is the following combinations: 10 mg and 10 mg, 10 mg and 120 mg or 10 mg and 90 mg.

Application Example 13

The drug-loading formulation of vitamin C and Rk4-type reverse micelle:

30 mg vitamin C and 180 mg Rk4-type reverse ginsenoside nano micelle in the example 12 are added to a 50 ml beaker and 2 ml absolute ethanol is added, then they are dissolved by vortex mixer and then filtered by 0.45 μm filter paper, concentrated under reduced pressure and dried, then a nano micelle encapsulating vitamin C has been obtained. By test, the drug-loading rate of ginsenoside nano micelle is at least 99.5% and after the obtained drug-loading micelle placed in olive oil solution for at least 10 hours, the encapsulation efficiency is still no less than 90%.

In addition to the above, the nano micelles encapsulating vitamin C nano micelle are prepared, in which the mass of drugs and ginsenoside micelle is the following combinations: 10 mg and 10 mg, 10 mg and 120 mg or 10 mg and 90 mg.

Application Example 14

The drug-loading formulation of vitamin C and Rg6-type reverse micelle:

30 mg vitamin C and 180 mg Rg6-type reverse ginsenoside nano micelle in the example 13 are added to a 50 ml beaker and 2 ml absolute ethanol is added, then they are dissolved by vortex mixer and then filtered by 0.45 μm filter paper, concentrated under reduced pressure and dried, then a nano micelle encapsulating vitamin C has been prepared. By test, the drug-loading rate of ginsenoside nano micelle is at least 99.5% and after the obtained drug-loading micelle placed in olive oil solution for at least 10 hours, the encapsulation efficiency is still no less than 90%.

In addition to the above, the nano micelles encapsulating vitamin C are prepared, in which the mass of drugs and ginsenoside micelle is the following combinations: 10 mg and 10 mg, 10 mg and 120 mg or 10 mg and 90 mg.

Application Example 15

The drug-loading formulation of vitamin C and R4/Rg6-type reverse micelle:

30 mg vitamin C and 180 mg R4/Rg6-type reverse ginsenoside nano micelle in the example 13 are added to a 50 ml beaker and 2 ml absolute ethanol is added, then they are dissolved by vortex mixer and then filtered by 0.45 μm filter paper, concentrated under reduced pressure and dried, then a nano micelle encapsulating vitamin C has been prepared. By test, the drug-loading rate of ginsenoside nano micelle is at least 99.5% and after the obtained drug-loading micelle placed in olive oil solution for at least 10 hours, the encapsulation efficiency is still no less than 90%.

In addition to the above, the nano micelles encapsulating vitamin C are prepared, in which the mass of drugs and ginsenoside micelle is the following combinations: 10 mg and 10 mg, 10 mg and 120 mg or 10 mg and 90 mg.

Application Example 16

The drug-loading formulation of vitamin C and Rg2/Rk4/Rg6-type reverse micelle:

30 mg vitamin C and 180 mg Rg2/Rk4/Rg6-type reverse ginsenoside nano micelle in the example 13 are added to a 50 ml beaker and 2 ml absolute ethanol is added, then they are dissolved by vortex mixer and then filtered by a 0.45 μm filter paper, concentrated under reduced pressure and dried, then a nano micelle encapsulating vitamin C has been prepared. By test, the drug-loading rate of ginsenoside nano micelle is at least 99.5% and after the obtained drug-loading micelle placed in olive oil solution for at least 10 hours, the encapsulation efficiency is still no less than 90%.

In addition to the above, the nano micelles encapsulating vitamin C are prepared, in which the mass of drugs and ginsenoside micelle is the following combinations: 10 mg and 10 mg, 10 mg and 120 mg or 10 mg and 90 mg.

Effect Example

The granularity determination of ginsenoside nano micelle and the particle determination of ginsenoside nano micelle and application examples:

1. The preparation of samples and determination methods of samples

Type of granulometer and analysis conditions are as follows: type ELS800; detection conditions: diameter 1855.3 nm; polydispersity 20994e-001; diffusion parameters 2.5347e-008; temperature 23.2° C.; the solvent is water; refractive index 0.9242; viscosity 0.9242; the light scattering intensity 6560 CPS.

Figure 7:
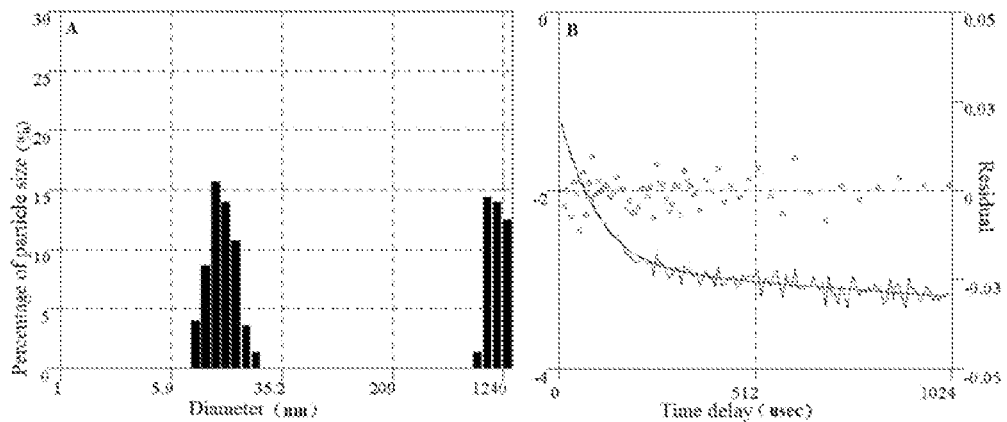
FIG. 7 is a size distribution figure of ginsenoside nano micelle it the example 1 in 5% glucose solution.

480 mg ginsenoside nano micelle in the example 1 is added to a 5 ml bottle and 2.0 ml absolute ethanol is added, it is stirred and dissolved by vortex mixer, filtered by 0.45 μm filter paper after dissolved, and 1 ml is taken and dissolved in 99 ml 5% glucose solution. The determination result obtained by the granulometer is shown in FIG. 7, and the data results are recorded in table 19.

TABLE 19

The granulometer results of ginsenoside nano micelle in the example 1

| Particle size (nm) | Proportion of the particle size (%) | Total proportion of below the particle size (%) |
|---|---|---|
| 8.2 | 4.0 | 4.0 |
| 9.6 | 8.6 | 12.6 |
| 11.3 | 15.6 | 78.3 |
| 13.3 | 14.0 | 42.3 |
| 15.7 | 10.7 | 52.9 |
| 18.4 | 3.6 | 56.6 |
| 21.7 | 1.3 | 57.9 |
| 763.0 | 1.3 | 59.2 |
| 897.0 | 14.3 | 73.5 |
| 1054.7 | 14.0 | 87.5 |
| 11240.0 | 12.5 | 100.0 |

Figure 8:
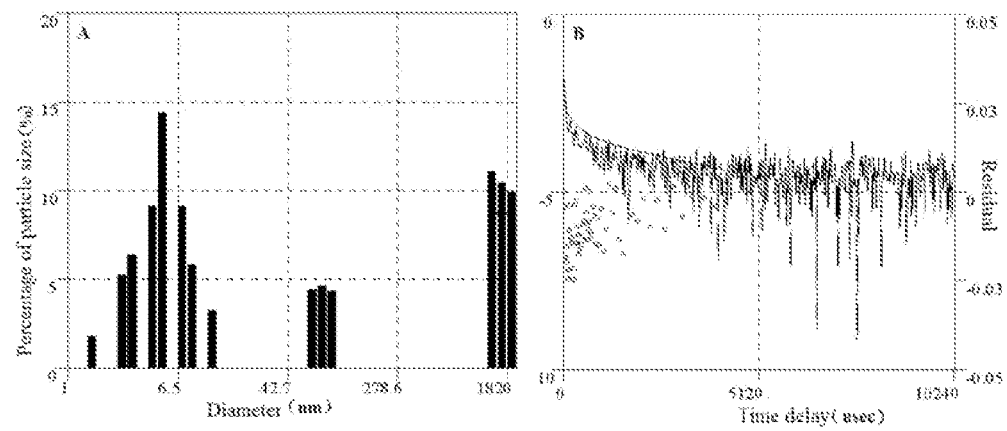
FIG. 8 is a size distribution figure of ginsenoside nano micelle an the example 2 in 5% glucose solution.

480 mg ginsenoside nano micelle in the example 2 is added into a 5 ml bottle and 2.0 ml ethanol is added, it is stared and dissolved by vortex mixer, filtered by 0.45 μm filter paper after dissolved, and 1 ml is taken and dissolved in 99 ml 5% glucose solution. The determination result obtained by the granulometer is shown in FIG. 8, and the data results are recorded in table 20.

TABLE 20

The granulometer results of ginsenoside nano micelle in the example 2

| Particle size (nm) | Proportion of the particle size (%) | Total proportion of below the particle size (%) |
|---|---|---|
| 1.4 | 1.8 | 1.8 |
| 2.3 | 5.2 | 7.0 |
| 2.8 | 6.4 | 13.4 |
| 3.9 | 9.1 | 22.6 |
| 4.6 | 14.4 | 36.9 |
| 6.5 | 9.1 | 46.1 |
| 7.7 | 5.8 | 51.9 |
| 10.9 | 3.2 | 55.1 |
| 1793.9 | 11.1 | 79.6 |
| 1534.5 | 10.5 | 90.1 |
| 1820.0 | 9.9 | 100.0 |

The determination result of the drug-loading micelle in the application example 1 obtained by granulometer is shown in FIG. 2, and the data results are recorded in table 21.

TABLE 21

The granulometer results of ginsenoside nano micelle in the application example 1

| Particle size (nm) | Proportion of the particle size (%) | Total proportion of below the particle size (%) |
|---|---|---|
| 7.7 | 0.8 | 0.8 |
| 98.1 | 5.1 | 5.9 |
| 116.2 | 16.3 | 22.1 |
| 137.7 | 27.1 | 49.2 |
| 163.2 | 27.9 | 77.2 |
| 193.5 | 17.0 | 94.2 |
| 229.3 | 5.8 | 100.0 |

The determination result of the drug-loading micelle in the application example 7 obtained by granulometer is shown in FIG. 4, and the data results are recorded in table 22.

TABLE 22

The granulometer results of ginsenoside nano micelle in the application example 7

| Particle size (nm) | Proportion of the particle size (%) | Total proportion of below the particle size (%) |
|---|---|---|
| 4.4 | 1.2 | 1.2 |
| 5.2 | 1.2 | 2.4 |
| 6.2 | 1.1 | 3.5 |
| 7.3 | 0.7 | 4.2 |
| 53.2 | 4.0 | 8.3 |
| 62.8 | 8.5 | 16.7 |
| 74.1 | 13.9 | 30.6 |
| 87.5 | 14.0 | 44.6 |
| 103.2 | 13.4 | 58.1 |
| 121.8 | 11.8 | 69.8 |
| 143.7 | 9.4 | 79.2 |
| 169.6 | 7.0 | 86.3 |
| 200.1 | 3.5 | 89.8 |
| 236.2 | 2.1 | 91.9 |
| 278.7 | 0.6 | 92.5 |
| 1048.4 | 2.5 | 95.0 |
| 1237.2 | 2.4 | 97.4 |
| 1460.0 | 2.6 | 100.0 |

The determination result of the drug-loading micelle in the application example 8 obtained by granulometer is shown in FIG. 5, and the data results are recorded in table 23.

TABLE 23

The granulometer results of ginsenoside nano micelle in the application example 8

| Particle size (nm) | Proportion of the particle size (%) | Total proportion of below the particle size (%) |
| --- | --- | --- |
| 6.1 | 1.0 | 1.0 |
| 7.3 | 3.6 | 4.6 |
| 8.6 | 7.3 | 11.9 |
| 10.1 | 10.0 | 21.8 |
| 11.9 | 10.7 | 32.6 |
| 14.0 | 9.3 | 41.8 |
| 16.6 | 6.9 | 48.8 |
| 19.5 | 3.8 | 52.6 |
| 23.0 | 1.3 | 53.8 |
| 323.5 | 0.6 | 55.2 |
| 381.6 | 0.8 | 56.0 |
| 450.1 | 2.3 | 58.3 |
| 531.0 | 3.1 | 61.4 |
| 626.3 | 5.7 | 67.1 |
| 738.7 | 5.4 | 72.4 |
| 871.4 | 5.0 | 77.4 |
| 1027.8 | 9.0 | 86.4 |
| 1212.3 | 7.4 | 93.8 |
| 1430.0 | 6.2 | 100.0 |

2. The performance parameters comparison result of the saponin nano micelle in the present invention and the common polymer micelle at present is shown in table 24:

TABLE 24 performance parameters comparison of saponin nano micelle and common polymer micelle

| Contrast projects | Polymer micelle | Saponin nano micelle |
| --- | --- | --- |
| Molecular weight | 10000~100000 | 2000-3000 |
| Raw material | Hydrophilic segments: Polyethylene glycol: Polymers of ethylene oxide and propylene oxide; Hydrophobic segments: poly (D, L-lactic acid), poly (lactide-glycolide), polycaprolactone | ginsenoside |
| Proportion of Drug/micelle | The mass ratio is 1%~20% | The mass ratio is 10%~50% |
| Drug Encapsulation efficiency | No less than 90% | The same as polymer micelle |
| Solubilization effect | dissolving indissolvable drugs, replacing Cremophor EL, tween 80 and other toxic solvents | The same as polymer micelle |
| Preparation methods of micelle | The preparation is relatively complex, using kinds of poisonous and harmful solvents and reagents, such as chloroform, dichloromethane, methanol, acetone, dimethyl sulfoxide, dimethyl formamide, acetonitrile | The preparation is simple, the technology is mature, can only use ethanol |
| Targeting property | Have certain targeting property | Have stronger targeting property |
| Anti-drug resistance | No | Have stronger anti-drug resistance |
| Toxicity | Non-toxic or low toxic | non-toxic |
| Micelle stability | Relatively stable | The same as polymer micelle |
| Drugs sustained-release ability | Have certain sustained-release ability | The same as polymer micelle |
| Drug synergism | No | Have stronger drug synergism |
| Improve immunity | No | Can greatly improve human immunity |

3. The micromorphology test of saponin nano micelle by JEM-1400-type transmission electron microscope:

180 mg ginsenoside nano micelle in the example 1, example 2 and example 5 and paclitaxel drug-loading ginsenoside nano micelle of the application example 1 is taken respectively, 2.5 mL ethanol dispersed is added to carry out dispersion by ultrasonic, and then each sample is tested by micromorphology, the test result of each sample is shown in FIG. 9~12.

Figure 9:
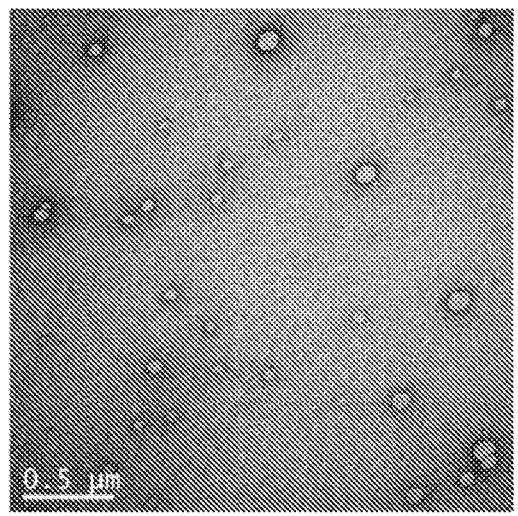
FIG. 9 is a transmission electron microscopy image of HSE-type ginsenoside nano micelle in the example 1.
Figure 10:
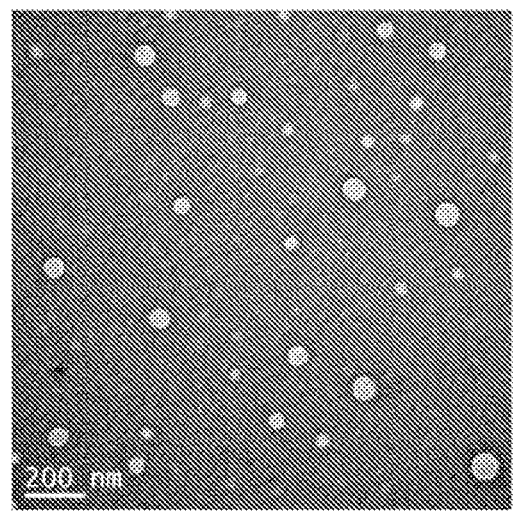
FIG. 10 is a transmission electron microscopy image of Rg3/Rg5/Rk1-type ginsenoside nano micelle in the example 2.
Figure 11:
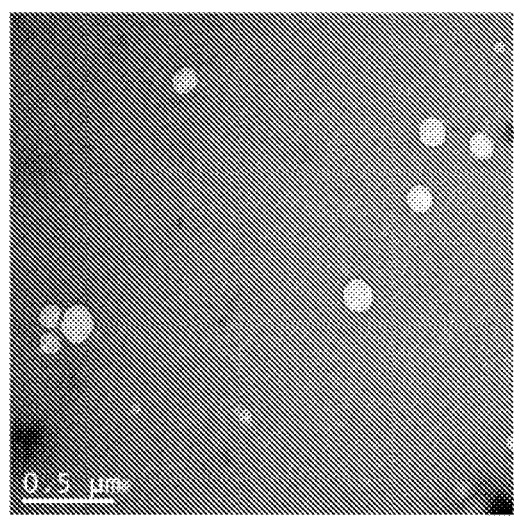
FIG. 11 is a transmission electron microscopy image of Rg2/Rk4/Rg6-type reverse ginsenoside nano micelle in the example 5.
Figure 12:
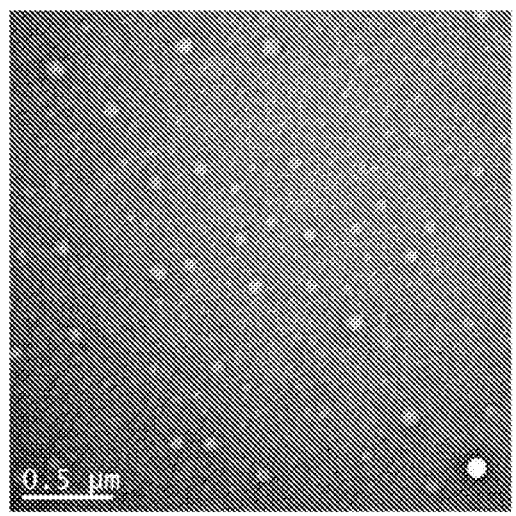
FIG. 12 is a transmission electron microscopy image of paclitaxel drug-loading ginsenoside nano micelle in the application example 1.

Wherein, FIG. 9 is a transmission electron microscopy image of HSE-type ginsenoside nano micelle in the example 1. FIG. 10 is a transmission electron microscopy image of Rg3/Rg5/Rk1-type ginsenoside nano micelle in the example 2. FIG. 11 is a transmission electron microscopy image of Rg2/Rk4/Rg6-type reverse ginsenoside nano micelle in the example 5. FIG. 12 is a transmission electron microscopy image of paclitaxel drug-loading ginsenoside nano micelle in the application example 1. It can be seen from the figures that the saponin nano micelle of the present invention is substantially spherical and has a normal micellar structure, and the structure is stable.

While specific embodiments of the present invention are described above, those skilled in this field should understand that these are only illustrative, on condition of without departing from the principles and spirit of the present invention, various alterations or modifications can be made to these embodiments. Therefore, the scope of protection of the invention is defined by the appended claims.

What is claimed is:

1. A saponin nano micelle, comprising one or more of saponins represented by Formula 1;

formula 1 wherein, $R_1$ and $R_2$ are independently —H or a hydrophilic group, $R_3$ is —H or —OH, $R_4$ is a lipophilic group.

2. The saponin nano micelle according to claim 1, wherein, the hydrophilic group is —OH, glycosyl, modified glycosyl, aliphatic acyl group, amino acid group, organic acid ester group or sulfate; the modified glycosyl is polymer modified glycosyl, aliphatic acyl group modified glycosyl, amino acid group modified glycosyl or organic acid ester group modified glycosyl;

and/or, $R_1$ and $R_2$ are not —H at the same time.

3. The saponin nano micelle according to claim 2, wherein, $R_1$ and $R_2$ are independently one of the following groups:

(1) —H, —OH; wherein, —H is hydrogen group, —OH is hydroxy group;

(2) $R_6$, wherein, $R_6$ is one of the following groups: —O-Glc, —O-Rha, —O-Lyx, —O-Xyl, —O-Ara(p), —O-Ara(f), —O-Glc(2→1)Glc, —O-Glc(6→1)Glc, —O-Glc(2→1)Rha, —O-Glc(2→1)Xyl, —O-Glc(6→1)Xyl, —O-Glc(6→1)Rha, —O-Glc(2→1)Ara(p), —O-Glc(6→1)Ara(p), —O-Glc(2→1)Ara(f), —O-Glc(6→1)Ara(f), —O-Glc(2→1)Glc(2→1)Glc, —O-Glc(2→1)Glc(2→1)Xyl, —O-Glc(6→1)Glc(6→1)Xyl, —O-Glc(2→1)Glc(4→1)Xyl, —O-Glc(2→1)Lyx, —O-Glc(2→1)Glc(2→1)Lyx, —O-Glc(2→1)Glc(2→1)Rha, —O-Glc(2→1)Glc(2→1)Lyx, —O-Glc(2→1)Glc(2→1)Ara(f), —O-Glc(2→1)Glc(2→1)Ara(p), —O-Glc(2→1)Glc(6→1)Glc, —O-Glc(2→1)Glc(6→1)Rha, —O-Glc(2→1)Glc(6→1)Xyl, —O-Glc(2→1)Glc(6→1)Lyx, —O-Glc(2→1)Glc(6→1)Ara(f), —O-Glc(2→1)Glc(6→1)Ara(p), —O-Glc(6→1)Glc(2→1)Glc, —O-Glc(6→1)Glc(2→1)Rha, —O-Glc(6→1)Glc(2→1)Xyl, —O-Glc(6→1)Glc(2→1)Lyx, —O-Glc(6→1)Glc(2→1)Ara(f), —O-Glc(6→1)Glc(2→1)Ara(p), —O-Glc(6→1)Glc(6→1)Glc, —O-Glc(6→1)Glc(6→1)Rha, —O-Glc(6→1)Glc(6→1)Xyl, —O-Glc(6→1)Glc(6→1)Lyx, —O-Glc(6→1)Glc(6→1)Ara(f), —O-Glc(6→1)Glc(6→1)Ara(p); wherein, Glc is glucopyranosyl, Xyl is xylopyranosyl, Rha is rhamnopyranosyl, Ara(p) is arabinopyranosyl, Ara(f) is arabinofuranosyl, Lyx is lyxose group;

(3) $R_7$, $R_7$ is a group formed when no less than one of hydroxyl in $R_6$ is replaced by $R_5$, wherein, $R_5$ is one of the following groups:

I) -mPEG, —Z-mPEG, -mPEO, —Z-PEO, -mPVP, —Z-PVP, -mEPEG or —Z-EPEG; wherein, m is H, alkyl or acyl, Z is —CO(CH$_2$)$_a$CO—, —NH(CH$_2$)$_a$CO—, —NH(CH$_2$)$_b$X— or —CO—Ar—CH$_2$—; wherein, X is O, S or NH, Ar is aryl, a is an integer from 1 to 8, b is an integer from 1 to 10;

II) straight chain aliphatic acyl having 4 to 22 carbon atoms, phosphate group, succinic acid ester group, n-butyl acid ester group, sulfonate group, malic acid ester group or sodium sulfate salt;

III) a group formed by dehydrogenizing carboxyl of one of Boc-glycine, Boc-alanine, Boc-Arginine, Boc-Lysine, Boc-Serine, Acetyl phenylalanine, Acetyl-proline, Acetyl phenylalanine, Asparagine, Aspartic acid, Cysteine, Glutamine, Glutamic acid, Histidine, Isoleucine, Leucine, Methionine, Phenylalanine, Proline, Threonine, Tryptophan, Tyrosine or Valine;

(4) —O-PEO, —O-PVP, —O-PEG, —O-MPEG, —O-EPEG, —O-Glc (2→1)Glc(6→1)Mal or —O-Glc (2→1)Glc(6→1)Ac; wherein, Mal is malonyl, Ac is acetyl, PEG is polyethylene glycol, PEO is polyoxyethylene, MPEG is end-monomethoxy polyethylene glycol, EPEG is end-epoxy polyethylene glycol, PVP is povidone;

(5) $R_8$, $R_8$ is one of the following groups:

I) —Z-mPEG, -mPEO, —Z-PEO, -mPVP, —Z-PVP, -mEPEG or —Z-EPEG; wherein, m is H, alkyl or acyl, Z is —CO(CH$_2$)$_a$CO—, —NH(CH$_2$)$_a$CO—, —NH(CH$_2$)$_b$X— or —CO—Ar—CH$_2$—; wherein, X is O, S or NH, Ar is aryl, a is an integer from 1 to 8, b is an integer from 1 to 10;

II) straight chain aliphatic acyl having 4 to 22 carbon atoms, phosphate group, succinic acid ester group, n-butyl acid ester group, sulfonate group, malic acid ester group or sodium sulfate salt;

III) a group formed by dehydrogenizing carboxyl of one of Boc-glycine, Boc-alanine, Boc-Arginine, Boc-Lysine, Boc-Serine, Acetyl phenylalanine, Acetyl-proline, Acetyl phenylalanine, Asparagine, Aspartic acid, Cysteine, Glutamine, Glutamic acid, Histidine, Isoleucine, Leucine, Methionine, Phenylalanine, Praline, Threonine, Tryptophan, Tyrosine or Valine;

and $R_1$ and $R_2$ are not —H at the same time.

4. The saponin nano micelle according to claim 3, wherein, the molecular weight of the PEG, PEO, PVP and EPEG is independently 200 to 20000; and/or, the straight chain aliphatic acyl group is stearyl or palmityl;

and/or, when $R_6$ is —O-Glc, —O-Rha, —O-Lyx, —O-Xyl, —O-Ara(p) or —O-Ara(f), $R_7$ is a group formed when 1 to 4 hydroxyls in $R_6$ are replaced by $R_5$; when $R_6$ is —O-Glc(2→1)Glc, —O-Glc(6→1)Glc, —O-Glc (2→1)Rha, —O-Glc(2→1)Xyl, —O-Glc(6→1)Xyl, —O-Glc(6→1)Rha, —O-Glc(2→1)Ara(p), —O-Glc (6→1)Ara(p), —O-Glc(2→1)Ara(f), —O-Glc(6→1) Ara(f), —O-Glc(2→1)Lyx or —O-Glc(6→1)Lyx, $R_7$ is a group formed when 1 to 7 hydroxyls in $R_6$ are replaced by $R_5$; when $R_6$ is —O-Glc (2→1)Glc(4→1)Xyl, —O-Glc(2→1)Glc(2→1)Rha, —O-Glc(2→1)Glc (2→1)Lyx, —O-Glc (2→1)Glc(2→1)Ara(f), —O-Glc (2→1)Glc(2→1)Ara(p), —O-Glc(2→1)Glc(6→1)Glc, —O-Glc(2→1)Glc(6→1)Rha, —O-Glc(2→1)Glc (6→1)Xyl, —O-Glc(2→1)Glc(6→1)Lyx, —O-Glc (2→1)Glc(6→1)Ara(f), —O-Glc(2→1)Glc(6→1)Ara (p), —O-Glc(6→1)Glc(2→1)Glc, —O-Glc(6→1)Glc (2→1)Rha, —O-Glc(6→1)Glc(2→1)Xyl, —O-Glc (6→1)Glc(2→1)Lyx, —O-Glc(6→1)Glc(2→1)Ara(f), —O-Glc(6→1)Glc(2→1)Ara(p), —O-Glc(6→1)Glc (6→1)Glc, —O-Glc(6→1)Glc(6→1)Rha, —O-Glc (6→1)Glc(6→1)Lyx, —O-Glc(6→1)Glc(6→1)Ara(f) or —O-Glc(6→1)Glc(6→1)Ara(p), $R_7$ is a group formed when 1 to 10 hydroxyls in $R_6$ are replaced by $R_5$.

5. The saponin nano micelle according to claim 1, wherein, $R_4$ is the group represented by Formula 2, Formula 3 or Formula 4;

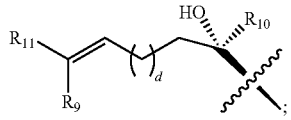

formula 2 wherein, $R_9$, $R_{10}$ and $R_{11}$ are independently alkyl having 1 to 3 carbon atoms, d is an integer from 1 to 3;

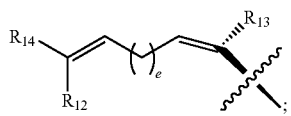

formula 3 wherein, $R_{12}$, $R_{13}$ and $R_{14}$ are independently alkyl having 1 to 3 carbon atoms, e is an integer from 1 to 3;

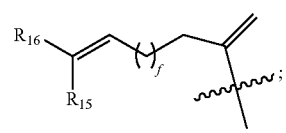

formula 4 wherein, $R_{15}$ and $R_{16}$ are independently $C_1$–$C_3$ alkyl, f is an integer from 1 to 3.

6. The saponin nano micelle according to claim 5, wherein, $R_4$ is the group represented by Formula 2-1, Formula 3-1 or Formula 4-1;

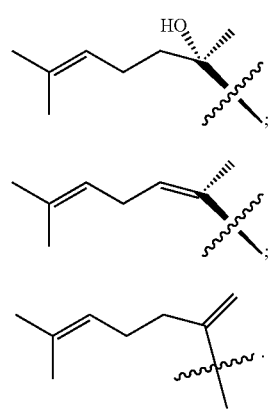

formula 2-1 formula 3-1 formula 4-1

7. The saponin nano micelle according to claim 1, wherein, the saponin nano micelle comprises a type A saponin, a type B saponin or a type C saponin; wherein, the type A saponin is represented by Formula 1-1, the type B saponin is represented by Formula 1-2, and the type C saponin is represented by Formula 1-3;

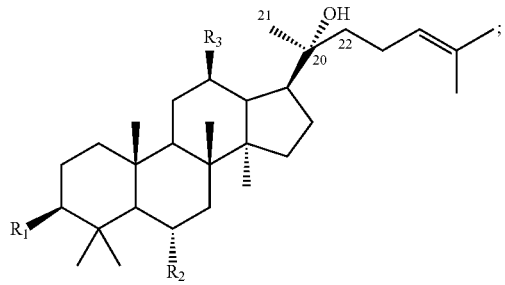

formula 1-1

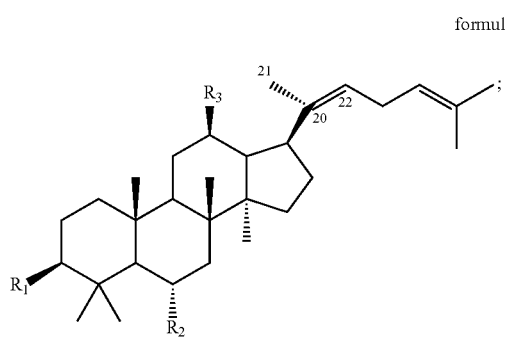

formula 1-2

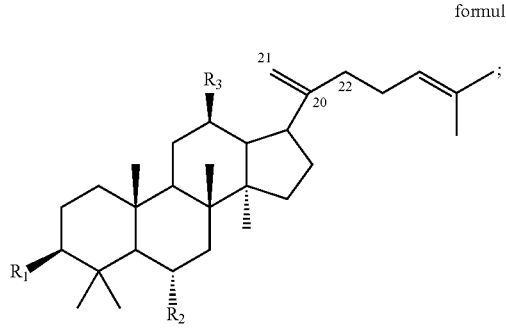

formula 1-3 a mass content of the saponin is no less than 70%;

or, the saponin nano micelle comprises the type B saponin or the type C saponin, a molar content of the saponin is no less than 70%.

8. The saponin nano micelle according to claim 1, wherein, the saponin nano micelle comprises any two kinds of saponins selected from the group consisting of a type A saponin, a type B saponin and a type C saponin; a mass content of the two kinds of saponins is respectively no less than 25%, a total mass content of the two kinds of saponins is no less than 70%;

or, the saponin nano micelle comprises the type B saponin and the type C saponin, a molar content of the type B saponin and the type C saponin is respectively no less than 25%, a total molar content of the type B saponin and the type C saponin is no less than 70%;

wherein, the type A saponin is represented by Formula 1-1, the type B saponin is represented by Formula 1-2, and the type C saponin is represented by Formula 1-3;

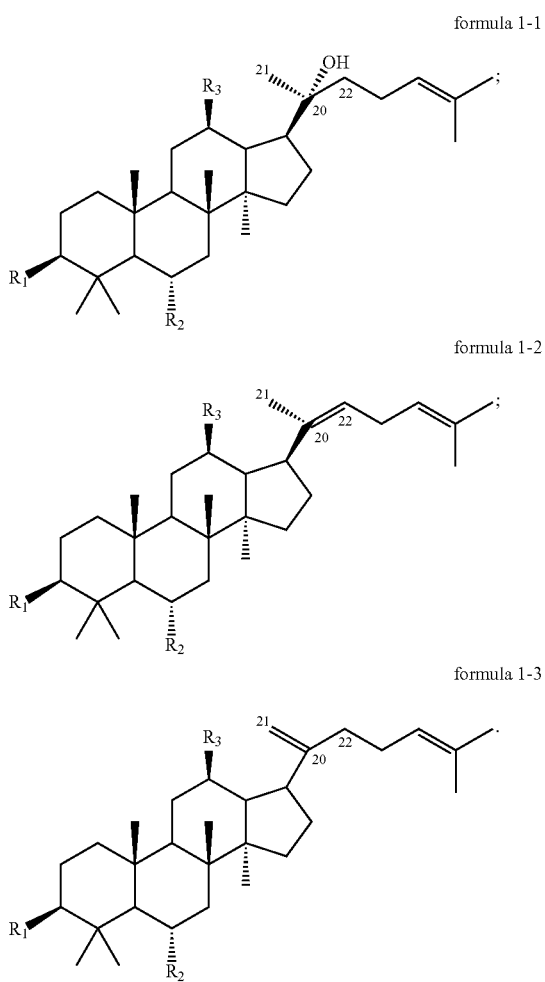

formula 1-1;

formula 1-2;

formula 1-3.

9. The saponin nano micelle according to claim 1, wherein the saponin nano micelle comprises a ginsenoside Rg5, a mass content of the ginsenoside Rg5 is no less than 50%; or, the saponin nano micelle comprises the ginsenoside Rg5, a molar content of the ginsenoside Rg5 is no less than 50%.

10. The saponin nano micelle according to claim 1, wherein the saponin nano micelle comprises a ginsenoside Rk1, a mass content of the ginsenoside Rk1 is no less than 50%;
or, the saponin nano micelle comprises the ginsenoside Rk1, a molar content of the ginsenoside Rk1 is no less than 50%.

11. The saponin nano micelle according to claim 1, wherein the saponin nano micelle comprises a ginsenoside Rk4, a mass content of the ginsenoside Rk4 is no less than 50%;
or, the saponin nano micelle comprises the ginsenoside Rk4, a molar content of the ginsenoside Rk4 is no less than 50%.

12. The saponin nano micelle according to claim 1, wherein the saponin nano micelle comprises ginsenoside Rg6, a mass content of ginsenoside Rg6 is no less than 50%;
or, the saponin nano micelle which comprises ginsenoside Rg6, a molar content of ginsenoside Rg6 is no less than 50%.

13. The saponin nano micelle according to claim 1, wherein the saponin nano micelle comprises a ginsenoside Rg5 and a ginsenoside Rk1, wherein a mass content of the ginsenoside Rg5 is no less than 15%, a mass content of the ginsenoside Rk1 is no less than 15%, and a total mass content of the ginsenoside Rg5 and the ginsenoside Rk1 is no less than 50%;
or, the saponin nano micelle comprises the ginsenoside Rg5 and the ginsenoside Rk1, wherein a molar content of the ginsenoside Rg5 is no less than 15%, a molar content of the ginsenoside Rk1 is no less than 15%, and a total molar content of the ginsenoside Rg5 and the ginsenoside Rk1 is no less than 50%.

14. The saponin nano micelle according to claim 1, wherein the saponin nano micelle comprises a ginsenoside Rk4 and a ginsenoside Rg6, wherein a mass content of the ginsenoside Rk4 is no less than 15%, a mass content of the ginsenoside Rg6 is no less than 15%, and a total mass content of the ginsenoside Rk4 and the ginsenoside Rg6 is no less than 50%;
or, the saponin nano micelle comprises the ginsenoside Rk4 and the ginsenoside Rg6, a molar content of the ginsenoside Rk4 is no less than 15%, a molar content of the ginsenoside Rg6 is no less than 15%, and a total molar content of the ginsenoside Rk4 and the ginsenoside Rg6 is no less than 50%.

15. A saponin nano micelle, wherein the saponin nano micelle comprises a ginsenoside (S)-Rg3, a ginsenoside Rg5 and a ginsenoside Rk1, wherein a mass content of the ginsenoside (S)-Rg3 is 15% to 45%, a mass content of the ginsenoside Rg5 is 15% to 45%, a mass content of the ginsenoside Rk1 is 15% to 45%, and a total mass content of the ginsenoside (S)-Rg3, the ginsenoside Rg5 and the ginsenoside Rk1 is no less than 70%;
or, the saponin nano micelle comprises the ginsenoside (S)-Rg3, the ginsenoside Rg5 and the ginsenoside Rk1, wherein a molar content of the ginsenoside (S)-Rg3 is 15% to 45%, a molar content of the ginsenoside Rg5 is 15% to 45%, a molar content of the ginsenoside Rk1 is 15% to 45%, and a total molar content of the ginsenoside (S)-Rg3, the ginsenoside Rg5 and the ginsenoside Rk1 is no less than 70%;
or, the saponin nano micelle comprises ginsenoside Rg2, ginsenoside Rk4 and ginsenoside Rg6, wherein a mass content of the ginsenoside Rg2 is 15% to 45%, a mass content of the ginsenoside Rk4 is 15% to 45%, a mass content of the ginsenoside Rg6 is 15% to 45%, and a total mass content of the ginsenoside Rg2, the ginsenoside Rk4 and the ginsenoside Rg6 is no less than 70%;
or, the saponin nano micelle comprises ginsenoside Rg2, ginsenoside Rk4 and ginsenoside Rg6, wherein a molar content of the ginsenoside Rg2 is 15% to 45%, a molar content of the ginsenoside Rk4 is 15% to 45%, a molar content of the ginsenoside Rg6 is 15% to 45%, and a total molar content of the ginsenoside Rg2, the ginsenoside Rk4 and the ginsenoside Rg6 is no less than 70%;
or, the saponin nano micelle comprises ginsenoside Rh2, ginsenoside Rh3 and ginsenoside Rk2, wherein a mass content of the ginsenoside Rh2 is 15% to 45%, a mass content of the ginsenoside Rh3 is 15% to 45%, a mass content of the ginsenoside Rk2 is 15% to 45%, and a total mass content of the ginsenoside Rh2, the ginsenoside Rh3 and the ginsenoside Rk2 is no less than 70%;
or, the saponin nano micelle comprises ginsenoside Rh2, ginsenoside Rh3 and ginsenoside Rk2, wherein a molar content of the ginsenoside Rh2 is 15% to 45%, a molar content of the ginsenoside Rh3 is 15% to 45%, a molar content of the ginsenoside Rk2 is 15% to 45%, and a total molar content of the ginsenoside Rh2, the ginsenoside Rh3 and the ginsenoside Rk2 is no less than 70%.

16. A process for preparing saponin nano micelle, comprising: mixing one or more of saponins represented by Formula 1 according to claim 1 with an organic solvent which can dissolve saponin, and then removing the organic solvent.

17. The process according to claim 16, wherein, the organic solvent which can dissolve saponin is selected from the group consisting of methanol, ethanol, N,N-dimethylformamide, n-butanol, propanol, tetrahydrofuran and pyridine; and/or, the mixing temperature is 30° C. to 80° C.; and/or, the way of removing the organic solvent is concentration and drying under reduced pressure at 30° C. to 80° C.

18. A process for preparing saponin nano micelle, comprising:
   (1) using an extract of plant of Araliaceae and/or Cucurbitaceae as raw materials, carrying out acidolysis reaction in an acidic aqueous solution to obtain a reaction solution containing a saponin mixture;
   (2) after purifying to remove impurities in the reaction solution containing the saponin mixture obtained in the step (1), mixing the resultant with an organic solvent which can dissolve saponin, and removing the organic solvent to obtain the saponin nano micelle;
   or, purifying and separating the reaction solution containing the saponin mixture obtained in the step (1) to obtain kinds of saponins, mixing one or more of saponins represented by Formula 1 according to claim 1, with an organic solvent which can dissolve saponin, and removing the organic solvent to obtain the saponin nano micelle.

19. The process according to claim 18, wherein, in the step (1), the plant of Araliaceae is selected from the group consisting of Chinese *ginseng* (*Panax ginseng*), Korean *ginseng* (*P. Sinensis J. Wen*), American *ginseng* (*P. quique folius*), Japanese *ginseng* (*P. japonicus*), Vietnamese *ginseng* (*P. vientnamesis*), *Panax* Pseudo-*ginseng* (*P. pseudoginseng*) and *Panax notoginseng* (*P. notoginseng*); and the plant of Cucurbitaceae is fiveleaf *gynostemma* herb (*Gynostemma pentaphyllum*);
   and/or, in the step (1), the extract of plant of Araliaceae and/or Cucurbitaceae satisfies the following conditions: a mass percentage content of total ginsenoside ≥60%; or containing any one of the following ginsenosides with the mass content ≥60%: ginsenoside Rb1, ginsenoside Rb2, ginsenoside Rb3, ginsenoside Re, ginsenoside Rc, ginsenoside Rd, ginsenoside Rg1, ginsenoside Rg2, ginsenoside Rg3, ginsenoside Rh1, ginsenoside Rh2, ginsenoside Rh3, ginsenoside F1, ginsenoside F2 and notoginsenoside R1;
   and/or, in the step (1), the acidic compound in the acidic aqueous solution is selected from the group consisting of citric acid, acetic acid, formic acid, oxalic acid, succinic acid, salicylic acid, tartaric acid, malic acid, citric acid, methanesulfonic acid, benzoic acid, hydrochloric acid, nitric acid, sulfuric acid and phosphoric acid;
   and/or, in the step (1), the pH value of the acidic aqueous solution is ≤6.5;
   and/or, in the step (1), the temperature of the acidolysis reaction is 60° C. to 100° C.; the time of the acidolysis reaction is 2 hours to 48 hours.

20. The process according to claim 18, wherein, the purifying to remove impurities comprises:
   (a) cooling the reaction solution containing the saponin mixture obtained in the step (1), settling, and removing sediment;
   (b) adjusting the pH of the reaction solution obtained by the step (a) to alkaline range by alkali to obtain a precipitate;
   (c) mixing the precipitate and an organic solvent at 30° C. to 80° C. to obtain a saponin mixture, the organic solvent is selected from the group consisting of methanol, ethanol, n-butanol, propanol, tetrahydrofuran and pyridine;
   (d) cooling the saponin mixture obtained in the step (c) to 5° C. below, removing sediment and drying;
   or, comprises:
   S1) adjusting the pH of the reaction solution containing saponin mixture obtained in the step (1) to pH 8 to 14 by alkali, removing sediment to obtain solution A;
   S2) extracting saponin in solution A obtained by the step S1 by n-butanol to obtain the n-butanol layer, then washing the n-butanol layer with water, and removing the solvent of the n-butanol layer.

21. The process according to claim 20, wherein, in the step (a), the cooling is to cool to −20° C. to 30° C., and the settling time is no less than 4 hours;
   and/or, in the step (b), the alkali is organic base and/or inorganic base;
   and/or, in the step (b), the way of adjusting the pH to alkaline is to adjust the pH to 8 to 14;
   and/or, in the step (b), the precipitate is dried, and then step (c) is conducted, and the way of drying is: drying at 30° C. to 80° C. until the weight loss on drying is less than 5% mass percentage;
   and/or, in the step (c), the usage of the organic solvent is an amount for dissolving the precipitate;
   and/or, in the step (c), the mixing temperature is 30° C. to 80° C.;
   and/or, in the step (d), the cooling temperature is −20° C. to 5° C.;
   and/or, in the step (d), the way of drying is concentration and drying under reduced pressure;
   and/or, in the step S1), the alkali is organic base and/or inorganic base;
   and/or, in the step S2), the number of extraction times is 1 to 5 times, the volume ratio of the n-butanol and the solution A is (1:0.5) to (1:4); a volume ratio of the n-butanol and the washing water is (1:0.5) to (1:4); the operation of removing the solvent of the n-butanol layer is concentration and drying under reduced pressure.

22. The process according to claim 18, wherein, in the step (2), the method of the purifying and separating is column chromatography;
   and/or, in the step (2), the saponin monomer is selected from the group consisting of ginsenoside Rg2, ginsenoside Rg3, ginsenoside Rg4, ginsenoside Rg5, ginsenoside Rg6, ginsenoside Rh1, ginsenoside Rh2, ginsenoside Rh3, ginsenoside Rh4, ginsenoside Rf, ginsenoside Rs3, ginsenoside Rk1, ginsenoside Rk2, ginsenoside Rk3, ginsenoside Rk4, ginsenoside, ginsenoside F4, notoginsenoside R2 and notoginsenoside T5.

23. The process according to claim 18, wherein, in the step (2), the organic solvent which can dissolve saponin is selected from the group consisting of methanol, ethanol, N,N-dimethylformamide, n-butanol, propanol, tetrahydrofuran and pyridine;
   and/or, in the step (2), the mixing temperature is 30° C. to 80° C.;
   and/or, in the step (2), the way of removing the organic solvent is concentration and drying under reduced pressure at 30° C. to 80° C.

24. The process according to claim 18, comprising:
   (1') mixing acetic acid, water and an extract of plant of Araliaceae and/or Cucurbitaceae in which a mass content of saponin is more than 60%, the dosage of the acetic acid is 4 mL/g to 6 mL/g extract of plant of Araliaceae and/or Cucurbitaceae, the concentration of the acid aqueous solution is 40% to 60% by volume; and then carrying out reaction at 80° C. to 90° C. for 3 hours to 5 hours, after the reaction, cooling the reaction solution, settling for 4 to 24 hours and removing sediment;

(2') neutralizing the reaction solution treated in the step (1') with Na$_2$CO$_3$ and settling to obtain a precipitate;

(3') mixing the precipitate obtained in the step (2') with absolute ethanol at 30° C. to 80° C., and then cooling to 5° C. below, settling for 4 hours to 24 hours, removing sediment, and then concentrating under reduced pressure to obtain a concentrate; repeating the operation aforementioned in the step (3') for 1 to 3 times;

(4') and then drying the concentrate obtained in the step (3'), to obtain the saponin nano micelle;

wherein, the saponin in the step (1') is one selected from the group consisting of total ginsenoside Ra0, total ginsenoside Ra1, total ginsenoside Ra2, total ginsenoside Ra3, ginsenoside Rb1, ginsenoside Malonyl-Rb1, ginsenoside Rb2, ginsenoside Malonyl-Rb2, ginsenoside Rb3, ginsenoside Malonyl-Rb3, ginsenoside Rg1, ginsenoside Malonyl-Rg1, ginsenoside Rc, ginsenoside Malonyl-Rc, ginsenoside F2, ginsenoside Re, ginsenoside Rd, ginsenoside Malonyl-Rd, American *ginseng* R1, ginsenoside Rs1, ginsenoside Rs2, notoginsenoside D, notoginsenoside K, notoginsenoside R1, notoginsenoside R3, notoginsenoside R4, notoginsenoside R6, notoginsenoside I, notoginsenoside Fa, notoginsenoside Fc, notoginsenoside Fd, notoginsenoside Fe, notoginsenoside T, notoginsenoside L, notoginsenoside O, notoginsenoside P, notoginsenoside Q, notoginsenoside S, gypenoside IX and gypenoside XVII.

25. The preparing method according to claim 18, comprising:

(1") mixing citric acid, water and an extract of plant of Araliaceae and/or Cucurbitaceae in which a mass content of saponin is more than 60%, the dosage of the citric acid is 4 mL/g to 6 mL/g extract of plant of Araliaceae and/or Cucurbitaceae, the concentration of the citric acid aqueous solution is 40% to 60% by volume; and then carrying out reaction at 80° C. to 90° C. for 3 hours to 6 hours;

(2") cooling the reaction solution obtained from the step (1") to 15° C. to 30° C., neutralizing the reaction solution with Na$_2$CO$_3$ and removing sediment to obtain solution A;

(3") mixing the solution A obtained in the step (2"), water and n-butanol, extracting and separating for 1 to 4 times;

(4") washing the n-butanol layer obtained in the step (3") with water for 1 to 3 times, concentrating under reduced pressure to obtain a solid;

(5") mixing the solid obtained in the step (4") with absolute ethanol at 55° C. to 65° C., and then cooling to 5° C. below, settling for 4 hours to 24 hours, removing sediment, and then concentrating under reduced pressure to obtain a concentrate; repeating the operation aforementioned in the step (5") for 1 to 3 times;

(6") drying the concentrate obtained in the step (5") to obtain the saponin nano micelle;

the saponin in the step (1") is selected from the group consisting of total ginsenoside Ra0, total ginsenoside Ra1, total ginsenoside Ra2, total ginsenoside Ra3, ginsenoside Rb1, ginsenoside Malonyl-Rb1, ginsenoside Rb2, ginsenoside Malonyl-Rb2, ginsenoside Rb3, ginsenoside Malonyl-Rb3, ginsenoside Rg1, ginsenoside Malonyl-Rg1, ginsenoside Rc, ginsenoside Malonyl-Rc, ginsenoside F2, ginsenoside Re, ginsenoside Rd, ginsenoside Malonyl-Rd, American *ginseng* R1, ginsenoside Rs1, ginsenoside Rs2, notoginsenoside D, notoginsenoside K, notoginsenoside R1, notoginsenoside R3, notoginsenoside R4, notoginsenoside R6, notoginsenoside I, notoginsenoside Fa, notoginsenoside Fc, notoginsenoside Fd, notoginsenoside Fe, notoginsenoside T, notoginsenoside L, notoginsenoside O, notoginsenoside P, notoginsenoside Q, notoginsenoside S, gypenoside IX and gypenoside XVII.

26. A process for preparing positive saponin nano micelle, comprising: mixing a reverse saponin nano micelle, an organic solvent which can dissolve saponin and a crystal seed of a positive saponin nano micelle, removing the organic solvent to obtain the positive saponin nano micelle; wherein, the positive saponin nano micelle consisting of one or more of saponin represented by Formula 1 according to claim 1, wherein R$_2$ is —H or —OH, and R$_1$ is hydrophilic group; the reverse saponin nano micelle is the saponin nano micelles according to claim 1 wherein the saponin nano micelles is a reverse saponin nano micelle, or the reverse saponin nano micelle comprising ginsenoside Rg2, ginsenoside Rk4 and ginsenoside Rg6.

27. A positive saponin nano micelle prepared by the process according to claim 26.

28. An solubilizer or a pharmaceutical carrier, comprising the saponin nano micelle according to claim 1, when the solubilizer or the pharmaceutical carrier is an aqueous solubilizer or a pharmaceutical carrier of a lipid-soluble compound or composition, the saponin nano micelle is a positive saponin nano micelle;

when the solubilizer or the pharmaceutical carrier is a lipidic solubilizer or a pharmaceutical carrier of a water-soluble compound or composition, the saponin nano micelle is a reverse saponin nano micelle.

29. A pharmaceutical composition, a health care composition or a cosmetics composition, comprising the saponin nano micelle according to claim 1, when the pharmaceutical composition, the health care composition or the cosmetics composition comprises a water-indissolvable active ingredient, the saponin nano micelle is a positive saponin nano micelle;

when the pharmaceutical composition, the health care composition or the cosmetics composition comprises a water-soluble active ingredient, the saponin nano micelle is a reverse saponin nano micelle.

30. The saponin nano micelle according to claim 15, wherein, when the saponin nano micelle comprises the ginsenoside (S)-Rg3, the ginsenoside Rg5 and the ginsenoside Rk1, a mass ratio of the ginsenoside (S)-Rg3, the ginsenoside Rg5 and the ginsenoside Rk1 is 0.8 to 1.2:1.8 to 2.2:0.8 to 1.2, or a molar ratio of the ginsenoside (S)-Rg3, the ginsenoside Rg5 and the ginsenoside Rk1 is 0.8 to 1.2: 1.8 to 2.2:0.8 to 1.2;

when the saponin nano micelle comprises the ginsenoside Rh2, the ginsenoside Rh3 and the ginsenoside Rk2; a mass ratio of the ginsenoside Rh2, the ginsenoside Rh3 and the ginsenoside Rk2 is 0.8 to 1.2:1.8 to 2.2:0.8 to 1.2, or a molar ratio of the ginsenoside Rh2, the ginsenoside Rh3 and the ginsenoside Rk2 is 0.8 to 1.2:1.8 to 2.2:0.8 to 1.2;

when the saponin nano micelle comprises the ginsenoside Rg2, the ginsenoside Rk4 and the ginsenoside Rg6; a mass ratio of the ginsenoside Rg2, the ginsenoside Rk4 and the ginsenoside Rg6 is 0.8 to 1.2:1.8 to 2.2:0.8 to 1.2, or a molar ratio of the ginsenoside Rg2, the ginsenoside Rk4 and the ginsenoside Rg6 is 0.8 to 1.2:1.8 to 2.2:0.8 to 1.2.

31. The process according to claim 16, wherein the saponins comprise ginsenoside (S)-Rg3, ginsenoside Rg5 and ginsenoside Rk1, or ginsenoside Rg2, ginsenoside Rk4 and ginsenoside Rg6, or ginsenoside Rh2, ginsenoside Rh3 and ginsenoside Rk2.

32. The process according to claim 18, wherein the saponins comprise ginsenoside (S)-Rg3, ginsenoside Rg5 and ginsenoside Rk1, or ginsenoside Rg2, ginsenoside Rk4 and ginsenoside Rg6, or ginsenoside Rh2, ginsenoside Rh3 and ginsenoside Rk2.

33. The solubilizer or pharmaceutical carrier according to claim 28, wherein the saponins comprise ginsenoside (S)-Rg3, ginsenoside Rg5 and ginsenoside Rk1, or ginsenoside Rg2, ginsenoside Rk4 and ginsenoside Rg6, or ginsenoside Rh2, ginsenoside Rh3 and ginsenoside Rk2.

34. The pharmaceutical composition, health care composition or cosmetics composition according to claim 29, wherein the saponins comprise ginsenoside (S)-Rg3, ginsenoside Rg5 and ginsenoside Rk1, or ginsenoside Rg2, ginsenoside Rk4 and ginsenoside Rg6, or ginsenoside Rh2, ginsenoside Rh3 and ginsenoside Rk2.

\* \* \* \* \*